US012440250B2

(12) United States Patent
Treace et al.

(10) Patent No.: US 12,440,250 B2
(45) **Date of Patent: *Oct. 14, 2025**

(54) MULTI-DIAMETER K-WIRE FOR ORTHOPEDIC APPLICATIONS

(71) Applicant: Treace Medical Concepts, Inc., Ponte Vedra, FL (US)

(72) Inventors: John T. Treace, Ponte Vedra Beach, FL (US); Sean F. Scanlan, Jacksonville, FL (US); Michael Stedham, Jacksonville, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/432,396

(22) Filed: Feb. 5, 2024

(65) Prior Publication Data

US 2024/0173056 A1 May 30, 2024

Related U.S. Application Data

(63) Continuation of application No. 17/018,422, filed on Sep. 11, 2020, now Pat. No. 11,890,039.

(Continued)

(51) Int. Cl.

| | |
|---|---|
| ***A61B 17/72*** | (2006.01) |
| ***A61B 17/84*** | (2006.01) |
| ***A61B 17/88*** | (2006.01) |

(52) U.S. Cl.

CPC ........ *A61B 17/7291* (2013.01); *A61B 17/848* (2013.01); *A61B 17/8875* (2013.01)

(58) Field of Classification Search

CPC .......... A61B 17/7291; A61B 2017/565; A61B 17/8861

See application file for complete search history.

(56) References Cited

U.S. PATENT DOCUMENTS

| | | |
|---|---|---|
| 3,664,022 A | 5/1972 | Small |
| 4,069,824 A | 1/1978 | Weinstock |

(Continued)

FOREIGN PATENT DOCUMENTS

| | | |
|---|---|---|
| AU | 2006252612 A1 | 12/2006 |
| AU | 2009227957 A1 | 10/2009 |

(Continued)

OTHER PUBLICATIONS

Vilex, "The Vilex Plate System," Brochure, 2011, 4 pages.

(Continued)

*Primary Examiner* — Julianna N Harvey

(74) *Attorney, Agent, or Firm* — Fredrikson & Byron, P.A.

(57) ABSTRACT

A multi-diameter fixation pin, such as a K-wire can be used during an orthopedic procedure. The multi-diameter fixation pin may include a leading diameter sized for the specific orthopedic procedure being undertaken and/or the size of the bone into which the fixation pin is being inserted. The multi-diameter fixation pin may include a trailing diameter different than the leading diameter. The trailing diameter may be sized for use with a specific sized powered driver. For example, in orthopedic procedures that involve inserting larger diameter pins and smaller diameter pins into bone(s), all pins used in the procedure may have a trailing diameter (e.g., the larger diameter or the smaller diameter) that allows the pins to be inserted with the same powered driver (e.g., the same attachment head) without needing different sized drivers or attachment heads for different sized pins.

11 Claims, 15 Drawing Sheets

Related U.S. Application Data

(60) Provisional application No. 62/900,391, filed on Sep. 13, 2019.

(56) References Cited

U.S. PATENT DOCUMENTS

| | | | |
|---|---|---|---|
| 4,159,716 | A | 7/1979 | Borchers |
| 4,187,840 | A | 2/1980 | Watanabe |
| 4,335,715 | A | 6/1982 | Kirkley |
| 4,338,927 | A | 7/1982 | Volkov et al. |
| 4,349,018 | A | 9/1982 | Chambers |
| 4,409,973 | A | 10/1983 | Neufeld |
| 4,440,168 | A | 4/1984 | Warren |
| 4,501,268 | A | 2/1985 | Comparetto |
| 4,502,474 | A | 3/1985 | Comparetto |
| 4,509,511 | A | 4/1985 | Neufeld |
| 4,565,191 | A | 1/1986 | Slocum |
| 4,570,624 | A | 2/1986 | Wu |
| 4,627,425 | A | 12/1986 | Reese |
| 4,628,919 | A | 12/1986 | Clyburn |
| 4,632,102 | A | 12/1986 | Comparetto |
| 4,664,102 | A | 5/1987 | Comparetto |
| 4,708,133 | A | 11/1987 | Comparetto |
| 4,736,737 | A | 4/1988 | Fargie et al. |
| 4,750,481 | A | 6/1988 | Reese |
| 4,754,746 | A | 7/1988 | Cox |
| 4,757,810 | A | 7/1988 | Reese |
| 4,895,141 | A | 1/1990 | Koeneman et al. |
| 4,952,214 | A | 8/1990 | Comparetto |
| 4,959,065 | A | 9/1990 | Arnett et al. |
| 4,959,066 | A | 9/1990 | Dunn et al. |
| 4,978,347 | A | 12/1990 | Ilizarov |
| 4,988,349 | A | 1/1991 | Pennig |
| 4,995,875 | A | 2/1991 | Coes |
| 5,021,056 | A | 6/1991 | Hofmann et al. |
| 5,035,698 | A | 7/1991 | Comparetto |
| 5,042,983 | A | 8/1991 | Rayhack |
| 5,049,149 | A | 9/1991 | Schmidt |
| 5,053,039 | A | 10/1991 | Hofmann et al. |
| 5,078,719 | A | 1/1992 | Schreiber |
| 5,112,334 | A | 5/1992 | Alchermes et al. |
| 5,147,364 | A | 9/1992 | Comparetto |
| 5,176,685 | A | 1/1993 | Rayhack |
| 5,207,676 | A | 5/1993 | Canadell et al. |
| 5,246,444 | A | 9/1993 | Schreiber |
| 5,254,119 | A | 10/1993 | Schreiber |
| 5,304,180 | A | 4/1994 | Slocum |
| 5,312,412 | A | 5/1994 | Whipple |
| 5,358,504 | A | 10/1994 | Paley et al. |
| 5,364,402 | A | 11/1994 | Mumme et al. |
| 5,374,271 | A | 12/1994 | Hwang |
| 5,413,579 | A | 5/1995 | Tom Du Toit |
| 5,417,694 | A | 5/1995 | Marik et al. |
| 5,449,360 | A | 9/1995 | Schreiber |
| 5,470,335 | A | 11/1995 | Du Toit |
| 5,490,854 | A | 2/1996 | Fisher et al. |
| 5,529,075 | A | 6/1996 | Clark |
| 5,540,695 | A | 7/1996 | Levy |
| 5,578,038 | A | 11/1996 | Slocum |
| 5,586,564 | A | 12/1996 | Barrett et al. |
| 5,601,565 | A | 2/1997 | Huebner |
| 5,613,969 | A | 3/1997 | Jenkins, Jr. |
| 5,620,442 | A | 4/1997 | Bailey et al. |
| 5,620,448 | A | 4/1997 | Puddu |
| 5,643,270 | A | 7/1997 | Combs |
| 5,667,510 | A | 9/1997 | Combs |
| 5,690,639 | A | 11/1997 | Lederer et al. |
| 5,702,396 | A | 12/1997 | Hoenig et al. |
| H1706 | H | 1/1998 | Mason |
| 5,709,686 | A | 1/1998 | Talos et al. |
| 5,709,687 | A | 1/1998 | Pennig |
| 5,722,978 | A | 3/1998 | Jenkins, Jr. |
| 5,749,875 | A | 5/1998 | Puddu |
| 5,779,709 | A | 7/1998 | Harris, Jr. et al. |
| 5,785,712 | A | 7/1998 | Runciman et al. |
| 5,788,695 | A | 8/1998 | Richardson |
| 5,803,924 | A | 9/1998 | Oni et al. |
| 5,810,822 | A | 9/1998 | Mortier |
| 5,843,085 | A | 12/1998 | Graser |
| 5,893,553 | A | 4/1999 | Pinkous |
| 5,911,724 | A | 6/1999 | Wehrli |
| 5,935,128 | A | 8/1999 | Carter et al. |
| 5,941,877 | A | 8/1999 | Viegas et al. |
| 5,951,556 | A | 9/1999 | Faccioli et al. |
| 5,980,526 | A | 11/1999 | Johnson et al. |
| 5,984,931 | A | 11/1999 | Greenfield |
| 6,007,535 | A | 12/1999 | Rayhack et al. |
| 6,027,504 | A | 2/2000 | Mcguire |
| 6,030,391 | A | 2/2000 | Brainard et al. |
| 6,110,174 | A | 8/2000 | Nichter |
| 6,162,223 | A | 12/2000 | Orsak et al. |
| 6,171,309 | B1 | 1/2001 | Huebner |
| 6,203,545 | B1 | 3/2001 | Stoffella |
| 6,248,109 | B1 | 6/2001 | Stoffella |
| 6,391,031 | B1 | 5/2002 | Toomey |
| 6,478,799 | B1 | 11/2002 | Williamson |
| 6,511,481 | B2 | 1/2003 | Von Hoffmann et al. |
| 6,540,746 | B1 | 4/2003 | Bhler et al. |
| 6,547,793 | B1 | 4/2003 | Mcguire |
| 6,676,662 | B1 | 1/2004 | Bagga et al. |
| 6,719,773 | B1 | 4/2004 | Boucher et al. |
| 6,743,233 | B1 | 6/2004 | Baldwin et al. |
| 6,755,838 | B2 | 6/2004 | Trnka |
| 6,786,909 | B1 | 9/2004 | Dransfeld et al. |
| 6,796,986 | B2 | 9/2004 | Duffner |
| 6,859,661 | B2 | 2/2005 | Tuke |
| 7,018,383 | B2 | 3/2006 | Mcguire |
| 7,033,361 | B2 | 4/2006 | Collazo |
| 7,037,309 | B2 | 5/2006 | Weil et al. |
| 7,097,647 | B2 | 8/2006 | Segler |
| 7,112,204 | B2 | 9/2006 | Justin et al. |
| 7,153,310 | B2 | 12/2006 | Ralph et al. |
| 7,175,667 | B2 | 2/2007 | Saunders et al. |
| 7,182,766 | B1 | 2/2007 | Mogul |
| 7,229,445 | B2 | 6/2007 | Hayeck et al. |
| 7,241,298 | B2 | 7/2007 | Nemec et al. |
| 7,282,054 | B2 | 10/2007 | Steffensmeier et al. |
| 7,344,538 | B2 | 3/2008 | Myerson et al. |
| 7,377,924 | B2 | 5/2008 | Raistrick et al. |
| 7,465,303 | B2 | 12/2008 | Riccione et al. |
| 7,537,596 | B2 | 5/2009 | Jensen |
| 7,540,874 | B2 | 6/2009 | Trumble et al. |
| 7,572,258 | B2 | 8/2009 | Stiernborg |
| 7,641,660 | B2 | 1/2010 | Lakin et al. |
| D610,257 | S | 2/2010 | Horton |
| 7,686,811 | B2 | 3/2010 | Byrd et al. |
| 7,691,108 | B2 | 4/2010 | Lavallee |
| 7,695,473 | B2 | 4/2010 | Ralph et al. |
| 7,763,026 | B2 | 7/2010 | Egger et al. |
| 7,785,355 | B2 | 8/2010 | Mohr et al. |
| D629,900 | S | 12/2010 | Fisher |
| 7,931,680 | B2 | 4/2011 | Myerson et al. |
| 7,967,823 | B2 | 6/2011 | Ammann et al. |
| 7,972,338 | B2 | 7/2011 | O'Brien |
| D646,389 | S | 10/2011 | Claypool et al. |
| 8,057,478 | B2 | 11/2011 | Kuczynski et al. |
| 8,062,301 | B2 | 11/2011 | Ammann et al. |
| D651,315 | S | 12/2011 | Bertoni et al. |
| D651,316 | S | 12/2011 | May et al. |
| 8,080,010 | B2 | 12/2011 | Schulz et al. |
| 8,083,746 | B2 | 12/2011 | Novak |
| 8,123,753 | B2 | 2/2012 | Poncet |
| 8,133,283 | B2 | 3/2012 | Wilson |
| 8,137,406 | B2 | 3/2012 | Novak et al. |
| 8,147,530 | B2 | 4/2012 | Strnad et al. |
| 8,162,996 | B2 | 4/2012 | Schelling |
| 8,167,918 | B2 | 5/2012 | Strnad et al. |
| 8,172,848 | B2 | 5/2012 | Tomko et al. |
| 8,172,884 | B2 | 5/2012 | Bouman |
| 8,172,886 | B2 | 5/2012 | Castaneda et al. |
| 8,177,819 | B2 | 5/2012 | Huebner et al. |
| 8,177,820 | B2 | 5/2012 | Anapliotis et al. |
| 8,177,822 | B2 | 5/2012 | Medoff |
| 8,192,441 | B2 | 6/2012 | Collazo |
| 8,197,487 | B2 | 6/2012 | Poncet et al. |

(56) References Cited

U.S. PATENT DOCUMENTS 8,231,623 B1 7/2012 Jordan
8,231,662 B2 7/2012 Huebner
8,231,663 B2 7/2012 Kay et al.
8,235,994 B2 8/2012 Hollawell
8,236,000 B2 8/2012 Ammann et al.
8,236,034 B2 8/2012 Binder et al.
8,241,338 B2 8/2012 Castaneda et al.
8,246,561 B1 8/2012 Agee et al.
8,246,661 B2 8/2012 Beutter et al.
D666,721 S 9/2012 Wright et al.
8,257,403 B2 9/2012 Den Hartog et al.
8,257,405 B2 9/2012 Haidukewych et al.
8,262,664 B2 9/2012 Justin et al.
8,277,459 B2 10/2012 Sand et al.
8,282,644 B2 10/2012 Edwards
8,282,645 B2 10/2012 Lawrence et al.
8,292,966 B2 10/2012 Morton
8,303,596 B2 11/2012 Plaky et al.
8,313,492 B2 11/2012 Wong et al.
8,323,289 B2 12/2012 Re
8,337,503 B2 12/2012 Lian
8,343,159 B2 1/2013 Bennett
8,377,105 B2 2/2013 Bscher
8,382,807 B2 2/2013 Austin et al.
8,398,687 B2 3/2013 Vasta et al.
8,403,966 B2 3/2013 Ralph et al.
D679,395 S 4/2013 Wright et al.
8,409,209 B2 4/2013 Ammann et al.
8,435,246 B2 5/2013 Fisher et al.
8,444,679 B2 5/2013 Ralph et al.
8,475,462 B2 7/2013 Thomas et al.
8,496,662 B2 7/2013 Novak et al.
8,496,690 B2 7/2013 Sixto et al.
8,512,339 B2 8/2013 Medoff et al.
8,518,045 B2 8/2013 Szanto
8,523,870 B2 9/2013 Green, II et al.
8,529,571 B2 9/2013 Horan et al.
8,529,608 B2 9/2013 Terrill et al.
8,540,777 B2 9/2013 Ammann et al.
8,545,508 B2 10/2013 Collazo
8,545,540 B2 10/2013 Castaneda et al.
D694,884 S 12/2013 Mooradian et al.
D695,402 S 12/2013 Dacosta et al.
8,652,142 B2 2/2014 Geissler
8,657,820 B2 2/2014 Kubiak et al.
D701,303 S 3/2014 Cook
8,672,945 B2 3/2014 Lavallee et al.
8,696,716 B2 4/2014 Kartalian et al.
8,702,715 B2 4/2014 Ammann et al.
8,702,762 B2 4/2014 Jacene et al.
D705,929 S 5/2014 Frey
8,715,363 B2 5/2014 Ratron et al.
8,728,084 B2 5/2014 Berelsman et al.
8,734,492 B2 5/2014 Mohr et al.
8,758,354 B2 6/2014 Habegger et al.
8,764,760 B2 7/2014 Metzger et al.
8,764,763 B2 7/2014 Wong et al.
8,764,807 B2 7/2014 Michel et al.
8,771,279 B2 7/2014 Philippon et al.
8,777,948 B2 7/2014 Bernsteiner
8,784,427 B2 7/2014 Fallin et al.
8,784,457 B2 7/2014 Graham
8,784,498 B2 7/2014 Scheland
8,795,286 B2 8/2014 Sand et al.
8,801,727 B2 8/2014 Chan et al.
8,808,303 B2 8/2014 Stemniski et al.
8,808,334 B2 8/2014 Strnad et al.
8,828,012 B2 9/2014 May et al.
8,828,063 B2 9/2014 Blitz et al.
8,834,532 B2 9/2014 Velikov et al.
8,834,537 B2 9/2014 Castaneda et al.
8,852,249 B2 10/2014 Ahrens et al.
8,858,602 B2 10/2014 Weiner et al.
8,882,778 B2 11/2014 Ranft
8,882,816 B2 11/2014 Kartalian et al.
8,888,785 B2 11/2014 Ammann et al.
8,888,824 B2 11/2014 Austin et al.
D720,456 S 12/2014 Dacosta et al.
8,900,247 B2 12/2014 Tseng et al.
8,906,026 B2 12/2014 Ammann et al.
8,940,026 B2 1/2015 Hilse et al.
8,940,029 B2 1/2015 Leung et al.
8,945,132 B2 2/2015 Play et al.
8,998,903 B2 4/2015 Price et al.
8,998,904 B2 4/2015 Zeetser et al.
9,023,052 B2 5/2015 Lietz et al.
9,044,250 B2 6/2015 Olsen et al.
9,060,822 B2 6/2015 Wright et al.
9,089,376 B2 7/2015 Medoff et al.
9,101,421 B2 8/2015 Blacklidge
9,107,715 B2 8/2015 Blitz et al.
9,113,920 B2 8/2015 Ammann et al.
9,138,244 B2 9/2015 Mebarak et al.
D740,424 S 10/2015 Dacosta et al.
9,149,313 B2 10/2015 Strnad et al.
9,220,515 B2 12/2015 Castaneda et al.
9,271,769 B2 3/2016 Batsch et al.
9,375,242 B2 6/2016 Worcel
D765,844 S 9/2016 Dacosta
D766,434 S 9/2016 Dacosta
D766,437 S 9/2016 Dacosta
D766,438 S 9/2016 Dacosta
D766,439 S 9/2016 Dacosta
9,452,057 B2 9/2016 Dacosta et al.
9,522,023 B2 12/2016 Haddad et al.
9,592,084 B2 3/2017 Grant
9,622,805 B2 4/2017 Santrock et al.
9,642,656 B2 5/2017 Kotuljac et al.
9,668,793 B2 6/2017 Gaudin
9,750,538 B2 9/2017 Soffiatti et al.
9,785,747 B2 10/2017 Geebelen
9,867,642 B2 1/2018 Simon
9,936,994 B2 4/2018 Smith et al.
9,980,760 B2 5/2018 Dacosta et al.
10,028,750 B2 7/2018 Rose
10,064,631 B2 9/2018 Dacosta et al.
10,159,499 B2 12/2018 Dacosta et al.
10,226,287 B2 3/2019 Langford et al.
10,238,437 B2 3/2019 Simon
10,245,088 B2 4/2019 Dayton et al.
10,292,713 B2 5/2019 Fallin et al.
10,327,829 B2 6/2019 Dacosta et al.
10,376,268 B2 8/2019 Fallin et al.
10,470,779 B2 11/2019 Fallin et al.
10,849,631 B2 12/2020 Hatch et al.
11,304,705 B2 4/2022 Fallin et al.
11,890,039 B1 * 2/2024 Treace ................. A61B 17/848
2002/0099381 A1 7/2002 Maroney
2002/0107519 A1 8/2002 Dixon et al.
2002/0165552 A1 11/2002 Duffner
2002/0198531 A1 12/2002 Millard et al.
2003/0060827 A1 3/2003 Coughln
2004/0010259 A1 1/2004 Keller et al.
2004/0039394 A1 2/2004 Conti et al.
2004/0097946 A1 5/2004 Dietzel et al.
2004/0116930 A1 6/2004 O'Driscoll et al.
2004/0138669 A1 7/2004 Horn
2005/0004676 A1 1/2005 Schon et al.
2005/0033430 A1 2/2005 Powers et al.
2005/0059978 A1 3/2005 Sherry et al.
2005/0070909 A1 3/2005 Egger et al.
2005/0075641 A1 4/2005 Singhatat et al.
2005/0101961 A1 5/2005 Huebner et al.
2005/0149042 A1 7/2005 Metzger
2005/0192578 A1 9/2005 Horst
2005/0228389 A1 10/2005 Stiernborg
2005/0251147 A1 11/2005 Novak
2005/0267482 A1 12/2005 Hyde
2005/0273112 A1 12/2005 Mcnamara
2006/0116679 A1 6/2006 Lutz et al.
2006/0129163 A1 6/2006 Mcguire
2006/0149264 A1 7/2006 Castaneda et al.
2006/0206044 A1 9/2006 Simon
2006/0217733 A1 9/2006 Plassky et al.

(56) References Cited

U.S. PATENT DOCUMENTS

| | | | |
|---|---|---|---|
| 2006/0229621 | A1 | 10/2006 | Cadmus |
| 2006/0235397 | A1 | 10/2006 | Sanders et al. |
| 2006/0241607 | A1 | 10/2006 | Myerson et al. |
| 2006/0241608 | A1 | 10/2006 | Myerson et al. |
| 2006/0264961 | A1 | 11/2006 | Murray-Brown |
| 2006/0276795 | A1 | 12/2006 | Orbay et al. |
| 2007/0010818 | A1 | 1/2007 | Stone et al. |
| 2007/0055249 | A1 | 3/2007 | Jensen et al. |
| 2007/0123857 | A1 | 5/2007 | Deffenbaugh et al. |
| 2007/0123884 | A1 | 5/2007 | Abdou |
| 2007/0191848 | A1 | 8/2007 | Wack et al. |
| 2007/0233138 | A1 | 10/2007 | Figueroa et al. |
| 2007/0265634 | A1 | 11/2007 | Weinstein |
| 2007/0276383 | A1 | 11/2007 | Rayhack |
| 2008/0009863 | A1 | 1/2008 | Bond et al. |
| 2008/0015591 | A1 | 1/2008 | Castaneda et al. |
| 2008/0015603 | A1 | 1/2008 | Collazo |
| 2008/0039850 | A1 | 2/2008 | Rowley et al. |
| 2008/0091197 | A1 | 4/2008 | Coughlin |
| 2008/0140081 | A1 | 6/2008 | Heavener et al. |
| 2008/0147073 | A1 | 6/2008 | Ammann et al. |
| 2008/0172054 | A1 | 7/2008 | Claypool et al. |
| 2008/0195215 | A1 | 8/2008 | Morton |
| 2008/0208252 | A1 | 8/2008 | Holmes |
| 2008/0262500 | A1 | 10/2008 | Collazo |
| 2008/0269908 | A1 | 10/2008 | Warburton |
| 2008/0288004 | A1 | 11/2008 | Schendel |
| 2009/0036893 | A1 | 2/2009 | Kartalian et al. |
| 2009/0036931 | A1 | 2/2009 | Pech et al. |
| 2009/0054899 | A1 | 2/2009 | Ammann et al. |
| 2009/0093849 | A1 | 4/2009 | Grabowski |
| 2009/0105767 | A1 | 4/2009 | Reiley |
| 2009/0118733 | A1 | 5/2009 | Orsak et al. |
| 2009/0118768 | A1 | 5/2009 | Sixto, Jr. et al. |
| 2009/0198244 | A1 | 8/2009 | Leibel |
| 2009/0198279 | A1 | 8/2009 | Zhang et al. |
| 2009/0210010 | A1 | 8/2009 | Strnad et al. |
| 2009/0210013 | A1 | 8/2009 | Kay et al. |
| 2009/0222047 | A1 | 9/2009 | Graham |
| 2009/0254092 | A1 | 10/2009 | Albiol Llorach |
| 2009/0254126 | A1 | 10/2009 | Orbay et al. |
| 2009/0281543 | A1 | 11/2009 | Orbay et al. |
| 2009/0287309 | A1 | 11/2009 | Walch et al. |
| 2010/0004691 | A1 | 1/2010 | Amato et al. |
| 2010/0023010 | A1 | 1/2010 | Nelson et al. |
| 2010/0069910 | A1 | 3/2010 | Hasselman |
| 2010/0121334 | A1 | 5/2010 | Couture et al. |
| 2010/0125300 | A1 | 5/2010 | Blitz et al. |
| 2010/0130981 | A1 | 5/2010 | Richards |
| 2010/0152752 | A1 | 6/2010 | Denove et al. |
| 2010/0152782 | A1 | 6/2010 | Stone et al. |
| 2010/0168799 | A1 | 7/2010 | Schumer |
| 2010/0185245 | A1 | 7/2010 | Paul et al. |
| 2010/0249779 | A1 | 9/2010 | Hotchkiss et al. |
| 2010/0256687 | A1 | 10/2010 | Neufeld et al. |
| 2010/0318088 | A1 | 12/2010 | Warne et al. |
| 2010/0324556 | A1 | 12/2010 | Tyber et al. |
| 2011/0008745 | A1 | 1/2011 | Mcquillan et al. |
| 2011/0009865 | A1 | 1/2011 | Orfaly |
| 2011/0087295 | A1 | 4/2011 | Kubiak et al. |
| 2011/0093017 | A1 | 4/2011 | Prasad et al. |
| 2011/0093084 | A1 | 4/2011 | Morton |
| 2011/0118739 | A1 | 5/2011 | Tyber et al. |
| 2011/0137351 | A1 | 6/2011 | Huebner et al. |
| 2011/0166607 | A1 | 7/2011 | Castaneda et al. |
| 2011/0178524 | A1 | 7/2011 | Lawrence et al. |
| 2011/0245835 | A1 | 10/2011 | Dodds et al. |
| 2011/0264149 | A1 | 10/2011 | Pappalardo et al. |
| 2011/0288550 | A1 | 11/2011 | Orbay et al. |
| 2011/0301648 | A1 | 12/2011 | Lofthouse et al. |
| 2011/0301653 | A1 | 12/2011 | Reed et al. |
| 2012/0016426 | A1 | 1/2012 | Robinson |
| 2012/0065689 | A1 | 3/2012 | Prasad et al. |
| 2012/0078258 | A1 | 3/2012 | Lo et al. |
| 2012/0123420 | A1 | 5/2012 | Honiball |
| 2012/0123484 | A1 | 5/2012 | Lietz et al. |
| 2012/0130376 | A1 | 5/2012 | Loring et al. |
| 2012/0130382 | A1 | 5/2012 | Iannotti et al. |
| 2012/0130383 | A1 | 5/2012 | Budoff |
| 2012/0184961 | A1 | 7/2012 | Johannaber |
| 2012/0185056 | A1 | 7/2012 | Warburton |
| 2012/0191199 | A1 | 7/2012 | Raemisch |
| 2012/0239045 | A1 | 9/2012 | Li |
| 2012/0253350 | A1 | 10/2012 | Anthony et al. |
| 2012/0265204 | A1 | 10/2012 | Schmierer et al. |
| 2012/0265301 | A1 | 10/2012 | Demers et al. |
| 2012/0277745 | A1 | 11/2012 | Lizee |
| 2012/0303033 | A1 | 11/2012 | Weiner et al. |
| 2012/0330135 | A1 | 12/2012 | Millahn et al. |
| 2013/0012949 | A1 | 1/2013 | Fallin et al. |
| 2013/0035694 | A1 | 2/2013 | Grimm et al. |
| 2013/0085499 | A1 | 4/2013 | Lian |
| 2013/0090695 | A1 | 4/2013 | Bernstein et al. |
| 2013/0096563 | A1 | 4/2013 | Meade et al. |
| 2013/0131821 | A1 | 5/2013 | Cachia |
| 2013/0150900 | A1 | 6/2013 | Haddad et al. |
| 2013/0150903 | A1 | 6/2013 | Vincent |
| 2013/0158556 | A1 | 6/2013 | Jones et al. |
| 2013/0165936 | A1 | 6/2013 | Myers |
| 2013/0165938 | A1 | 6/2013 | Chow et al. |
| 2013/0172942 | A1 | 7/2013 | Wright et al. |
| 2013/0184714 | A1 | 7/2013 | Kaneyama et al. |
| 2013/0190765 | A1 | 7/2013 | Harris et al. |
| 2013/0190766 | A1 | 7/2013 | Harris et al. |
| 2013/0204259 | A1 | 8/2013 | Zajac |
| 2013/0226248 | A1 | 8/2013 | Hatch et al. |
| 2013/0226252 | A1 | 8/2013 | Mayer |
| 2013/0231668 | A1 | 9/2013 | Olsen et al. |
| 2013/0237987 | A1 | 9/2013 | Graham |
| 2013/0237989 | A1 | 9/2013 | Bonutti |
| 2013/0238032 | A1 | 9/2013 | Schilter |
| 2013/0238093 | A1 | 9/2013 | Mauldin et al. |
| 2013/0261670 | A1 | 10/2013 | Laeng et al. |
| 2013/0267956 | A1 | 10/2013 | Terrill et al. |
| 2013/0310836 | A1 | 11/2013 | Raub et al. |
| 2013/0325019 | A1 | 12/2013 | Thomas et al. |
| 2013/0325076 | A1 | 12/2013 | Palmer et al. |
| 2013/0331845 | A1 | 12/2013 | Horan et al. |
| 2013/0338785 | A1 | 12/2013 | Wong |
| 2014/0005672 | A1 | 1/2014 | Edwards et al. |
| 2014/0012887 | A1 | 1/2014 | Tamano |
| 2014/0025127 | A1 | 1/2014 | Richter |
| 2014/0039501 | A1 | 2/2014 | Schickendantz et al. |
| 2014/0039561 | A1 | 2/2014 | Weiner et al. |
| 2014/0046387 | A1 | 2/2014 | Waizenegger |
| 2014/0052193 | A1 | 2/2014 | Prandi et al. |
| 2014/0074099 | A1 | 3/2014 | Vigneron et al. |
| 2014/0074101 | A1 | 3/2014 | Collazo |
| 2014/0081341 | A1 | 3/2014 | Lin et al. |
| 2014/0094861 | A1 | 4/2014 | Fallin |
| 2014/0094924 | A1 | 4/2014 | Hacking et al. |
| 2014/0107650 | A1 | 4/2014 | Dacosta et al. |
| 2014/0107798 | A1 | 4/2014 | Jeng et al. |
| 2014/0135775 | A1 | 5/2014 | Maxson et al. |
| 2014/0163563 | A1 | 6/2014 | Reynolds et al. |
| 2014/0171953 | A1 | 6/2014 | Gonzalvez et al. |
| 2014/0172021 | A1 | 6/2014 | Castaneda et al. |
| 2014/0180342 | A1 | 6/2014 | Lowery et al. |
| 2014/0180343 | A1 | 6/2014 | Gaudin |
| 2014/0188139 | A1 | 7/2014 | Fallin et al. |
| 2014/0194884 | A1 | 7/2014 | Martin et al. |
| 2014/0194999 | A1 | 7/2014 | Orbay et al. |
| 2014/0207144 | A1 | 7/2014 | Lee et al. |
| 2014/0214093 | A1 | 7/2014 | Courtney et al. |
| 2014/0249537 | A1 | 9/2014 | Wong et al. |
| 2014/0257291 | A1 | 9/2014 | Houff |
| 2014/0257308 | A1 | 9/2014 | Johannaber |
| 2014/0257509 | A1 | 9/2014 | Dacosta et al. |
| 2014/0276815 | A1 | 9/2014 | Riccione |
| 2014/0276853 | A1 | 9/2014 | Long et al. |
| 2014/0277176 | A1 | 9/2014 | Buchanan et al. |
| 2014/0277214 | A1 | 9/2014 | Helenbolt et al. |
| 2014/0288562 | A1 | 9/2014 | Von Zabern et al. |
| 2014/0296995 | A1 | 10/2014 | Reiley et al. |

(56) References Cited

U.S. PATENT DOCUMENTS

| | | | |
|---|---|---|---|
| 2014/0303621 | A1 | 10/2014 | Gerold et al. |
| 2014/0336658 | A1 | 11/2014 | Luna et al. |
| 2014/0343555 | A1 | 11/2014 | Russi et al. |
| 2014/0350561 | A1 | 11/2014 | Dacosta et al. |
| 2015/0032168 | A1 | 1/2015 | Orsak et al. |
| 2015/0039033 | A1 | 2/2015 | Biedermann |
| 2015/0045801 | A1 | 2/2015 | Axelson, Jr. et al. |
| 2015/0045839 | A1 | 2/2015 | Dacosta et al. |
| 2015/0051650 | A1 | 2/2015 | Verstreken et al. |
| 2015/0057667 | A1 | 2/2015 | Ammann et al. |
| 2015/0066094 | A1 | 3/2015 | Anderson et al. |
| 2015/0112446 | A1 | 4/2015 | Melamed et al. |
| 2015/0119944 | A1 | 4/2015 | Geldwert |
| 2015/0142064 | A1 | 5/2015 | Perez et al. |
| 2015/0150608 | A1 | 6/2015 | Sammarco |
| 2015/0182273 | A1 | 7/2015 | Stemniski et al. |
| 2015/0223851 | A1 | 8/2015 | Hill et al. |
| 2015/0245858 | A1 | 9/2015 | Weiner et al. |
| 2015/0313652 | A1 | 11/2015 | Burckhardt et al. |
| 2015/0335366 | A1 | 11/2015 | Dacosta et al. |
| 2015/0359580 | A1 | 12/2015 | Dacosta et al. |
| 2016/0015426 | A1 | 1/2016 | Dayton |
| 2016/0022315 | A1 | 1/2016 | Soffiatti et al. |
| 2016/0030098 | A1 | 2/2016 | Dacosta et al. |
| 2016/0030106 | A1 | 2/2016 | Carter et al. |
| 2016/0135858 | A1 | 5/2016 | Dacosta et al. |
| 2016/0151165 | A1 | 6/2016 | Fallin et al. |
| 2016/0175089 | A1 | 6/2016 | Fallin et al. |
| 2016/0192950 | A1 | 7/2016 | Dayton et al. |
| 2016/0192970 | A1 | 7/2016 | Dayton et al. |
| 2016/0199076 | A1 | 7/2016 | Fallin et al. |
| 2016/0213384 | A1 | 7/2016 | Fallin et al. |
| 2016/0235414 | A1 | 8/2016 | Hatch et al. |
| 2016/0235454 | A1 | 8/2016 | Treace et al. |
| 2016/0242791 | A1 | 8/2016 | Fallin et al. |
| 2016/0256204 | A1 | 9/2016 | Patel et al. |
| 2016/0324532 | A1 | 11/2016 | Montoya et al. |
| 2016/0354127 | A1 | 12/2016 | Lundquist et al. |
| 2017/0014143 | A1 | 1/2017 | Dayton et al. |
| 2017/0014173 | A1* | 1/2017 | Smith ................ A61B 17/1775 |
| 2017/0042598 | A1 | 2/2017 | Santrock et al. |
| 2017/0042599 | A1 | 2/2017 | Bays et al. |
| 2017/0079669 | A1 | 3/2017 | Bays et al. |
| 2017/0143511 | A1 | 5/2017 | Cachia |
| 2017/0164989 | A1 | 6/2017 | Weiner et al. |
| 2018/0132868 | A1 | 5/2018 | Dacosta et al. |
| 2018/0140339 | A1 | 5/2018 | Silva et al. |
| 2018/0344334 | A1 | 12/2018 | Kim et al. |
| 2018/0344371 | A1 | 12/2018 | Monk et al. |
| 2019/0357950 | A1 | 11/2019 | Bernstein et al. |
| 2020/0015856 | A1 | 1/2020 | Treace et al. |
| 2020/0015870 | A1 | 1/2020 | Treace |
| 2020/0281637 | A1 | 9/2020 | Denham |
| 2021/0022879 | A1 | 1/2021 | Hollis et al. |
| 2021/0282828 | A1 | 9/2021 | Champagne et al. |

FOREIGN PATENT DOCUMENTS

| | | | |
|---|---|---|---|
| CA | 2491824 | A1 | 9/2005 |
| CA | 2715491 | A1 | 8/2009 |
| CA | 2854997 | A1 | 5/2013 |
| CH | 695846 | A5 | 9/2006 |
| CN | 2701408 | Y | 5/2005 |
| CN | 2930668 | Y | 8/2007 |
| CN | 101237835 | A | 8/2008 |
| CN | 201558162 | U | 8/2010 |
| CN | 101836888 | A | 9/2010 |
| CN | 201572172 | U | 9/2010 |
| CN | 201586060 | U | 9/2010 |
| CN | 201912210 | U | 8/2011 |
| CN | 102755186 | A | 10/2012 |
| CN | 102860860 | A | 1/2013 |
| CN | 202801773 | U | 3/2013 |
| CN | 103462675 | A | 12/2013 |
| CN | 103505276 | A | 1/2014 |
| CN | 203458450 | U | 3/2014 |
| CN | 203576647 | U | 5/2014 |
| CN | 103892954 | A | 7/2014 |
| CN | 104490460 | A | 4/2015 |
| CN | 104510523 | A | 4/2015 |
| CN | 104523327 | A | 4/2015 |
| CN | 104546102 | A | 4/2015 |
| CN | 204379413 | U | 6/2015 |
| CN | 204410951 | U | 6/2015 |
| CN | 204428143 | U | 7/2015 |
| CN | 204428144 | U | 7/2015 |
| CN | 204428145 | U | 7/2015 |
| CN | 204446081 | U | 7/2015 |
| DE | 202006010241 | U1 | 3/2007 |
| DE | 102007053058 | B3 | 4/2009 |
| EP | 685206 | A1 | 12/1995 |
| EP | 1508316 | A1 | 2/2005 |
| EP | 1897509 | A1 | 3/2008 |
| EP | 2124772 | A1 | 12/2009 |
| EP | 2124832 | A2 | 12/2009 |
| EP | 2389884 | A1 | 11/2011 |
| EP | 2441406 | A1 | 4/2012 |
| EP | 2624764 | A1 | 8/2013 |
| EP | 2632349 | A1 | 9/2013 |
| EP | 2665428 | A1 | 11/2013 |
| EP | 2742878 | A1 | 6/2014 |
| EP | 2750617 | A1 | 7/2014 |
| EP | 2849684 | A1 | 3/2015 |
| EP | 3023068 | A2 | 5/2016 |
| ES | 2379929 | T3 | 5/2012 |
| FR | 2362616 | A1 | 3/1978 |
| FR | 2764183 | A1 | 12/1998 |
| FR | 2953120 | A1 | 6/2011 |
| FR | 3030221 | A1 | 6/2016 |
| GB | 2154143 | A | 9/1985 |
| GB | 2154144 | A | 9/1985 |
| GB | 2334214 | A | 8/1999 |
| IL | 184773 | A | 8/2012 |
| IN | 140/DELNP/2012 | P1 | 2/2013 |
| IN | 2004/KOLNP/2013 | P2 | 11/2013 |
| JP | 56028875 | U | 3/1981 |
| JP | S635739 | A | 1/1988 |
| JP | H07313522 | A | 12/1995 |
| JP | 2004174265 | A | 6/2004 |
| JP | 2006158972 | A | 6/2006 |
| JP | 4134243 | B2 | 8/2008 |
| JP | 4162380 | B2 | 10/2008 |
| JP | 2011092405 | A | 5/2011 |
| JP | 2011523889 | A | 8/2011 |
| JP | 4796943 | B2 | 10/2011 |
| JP | 5466647 | B2 | 4/2014 |
| JP | 2014511207 | A | 5/2014 |
| JP | 2014521384 | A | 8/2014 |
| JP | 5628875 | B2 | 11/2014 |
| KR | 100904142 | B1 | 6/2009 |
| KR | 101081268 | B1 | 11/2011 |
| MD | 756 | B1 | 7/1997 |
| RU | 2098036 | C1 | 12/1997 |
| RU | 2195892 | C2 | 1/2003 |
| RU | 2320287 | C1 | 3/2008 |
| RU | 2321366 | C2 | 4/2008 |
| RU | 2321369 | C1 | 4/2008 |
| RU | 2346663 | C2 | 2/2009 |
| RU | 2412662 | C1 | 2/2011 |
| SU | 1333328 | A2 | 8/1987 |
| WO | 0166022 | A1 | 9/2001 |
| WO | 03075775 | A1 | 9/2003 |
| WO | 2004024009 | A1 | 3/2004 |
| WO | 2004089227 | A2 | 10/2004 |
| WO | 2006065512 | A1 | 6/2006 |
| WO | 2007006430 | A1 | 1/2007 |
| WO | 2007106962 | A1 | 9/2007 |
| WO | 2008029142 | A2 | 3/2008 |
| WO | 2008029143 | A2 | 3/2008 |
| WO | 2008051064 | A1 | 5/2008 |
| WO | 2009029798 | A1 | 3/2009 |
| WO | 2009032101 | A2 | 3/2009 |
| WO | 2011037885 | A1 | 3/2011 |
| WO | 2012029008 | A1 | 3/2012 |

(56) References Cited

FOREIGN PATENT DOCUMENTS

| | | | |
|---|---|---|---|
| WO | 2013090392 | A1 | 6/2013 |
| WO | 2013134387 | A1 | 9/2013 |
| WO | 2013169475 | A1 | 11/2013 |
| WO | 2014020561 | A1 | 2/2014 |
| WO | 2014022055 | A1 | 2/2014 |
| WO | 2014035991 | A1 | 3/2014 |
| WO | 2014085882 | A1 | 6/2014 |
| WO | 2014147099 | A1 | 9/2014 |
| WO | 2014152219 | A2 | 9/2014 |
| WO | 2014152535 | A1 | 9/2014 |
| WO | 2014177783 | A1 | 11/2014 |
| WO | 2014200017 | A1 | 12/2014 |
| WO | 2015094409 | A1 | 6/2015 |
| WO | 2015094410 | A1 | 6/2015 |
| WO | 2015105880 | A1 | 7/2015 |
| WO | 2015127515 | A2 | 9/2015 |
| WO | 2016003477 | A1 | 1/2016 |
| WO | 2016134160 | A1 | 8/2016 |
| WO | 2017205512 | A1 | 11/2017 |
| ZA | 200808914 | A | 2/2012 |

OTHER PUBLICATIONS

"Speed Continuous Active Compression Implant," BioMedical Enterprises, Inc., AI20-029 Rev. 3, 2013, 4 pages.

Tornier, "CalcLock Extreme," Retrieved from< http://www.tornierus.com/lower/foot/footraO I I/>, 2014, 2 pages.

Zimmer, Inc. "Foot and Ankle Solutions," Retrieved from <http://www.zimmer.com/medical-professionals/products/foot-and-ankle.html>, 2014, 3 pages.

Wright Medical Group N.V., "Darco Modular Rearfoot System (MRS) LPS Lapidus Plating System," Brochure, Aug. 2016, 1 page.

Wright Medical Group N.V., "Foot & Ankle," Retrieved from<http://www.wright.com/physicians/foot-ankle>, 2016, 4 pages.

Mizuno et al., "Detorsion Osteotomy of the First Metatarsal Bone in Hallux Valgus," Japanese Orthopaedic Association, Tokyo, 1956; 30:813-819.

D'Amico et al., "Motion of the First Ray: Clarification Through Investigation," Journal of the American Podiatry Association, vol. 69, No. 1, Jan. 1979, pp. 17-23.

Eustace et al., "Hallux valgus, first metatarsal pronation and collapse of the medial longitudinal arch-a radiological correlation," Skeletal Radiology, vol. 23, 1994, pp. 191-194.

Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.

Easley et al., "Current Concepts Review: Hallux Valgus Part I: Pathomechanics, Clinical Assessment, and Nonoperative Management," Foot and Ankle International, vol. 28, No. 5, May 2007, pp. 654-659.

Easley et al., "Current Concepts Review: Hallux Valgus Part II: Operative Treatment," Foot and Ankle International, vol. 28, No. 6, Jun. 2007, pp. 748-758.

Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.

Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.

Easley et al., "What is the Best Treatment for Hallux Valgus?," Evidence-Based Orthopedics: The Best Answers to Clinical Questions, Chapter 73, 2009, pp. 479-491.

Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.

Dayton et al., "The Extended Knee Hemilithotomy Position for Gastrocnemius Recession," The Journal of Foot and Ankle Surgery, vol. 49, 2010, pp. 214-216.

Coetzee et al., "Revision Hallux Valgus Correction," Operative Techniques in Foot and Ankle Surgery, Section I, Chapter 15, 2011, pp. 84-96.

Dayton et al., "A User-Friendly Method of Pin Site Management for External Fixators," Foot and Ankle Specialist, Sep. 16, 2011, 4 pages.

Dayton et al., "Hallux Varus as Complication of Foot Compartment Syndrome," The Journal of Foot and Ankle Surgery, vol. 50, 2011, pp. 504-506.

Dayton et al., "Measurement of Mid-Calcaneal Length on Plain Radiographs: Reliability of a New Method," Foot and Ankle Specialist, vol. 4, No. 5, Oct. 2011, pp. 280-283.

Le et al., "Tarsometatarsal Arthrodesis," Operative Techniques in Foot and Ankle Surgery, Section II, Chapter 40, 2011, pp. 281-285.

Shurnas et al., "Proximal Metatarsal Opening Wedge Osteotomy," Operative Techniques in Foot and Ankle Surgery, Section I, Chapter 13, 2011, pp. 73-78.

Wienke et al., "Bone Stimulation for Nonunions: What the Evidence Reveals," Podiatry Today, vol. 24, No. 9, Sep. 2011, pp. 52-57.

Kim et Jal., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.

Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.

Colian et al., "The biomechanics of the first metatarsal bone in hallux valgus: A preliminary study utilizing a weight bearing extremity CT," Foot and Ankle Surgery, vol. 19, 2013, pp. 155-161.

Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.

Dayton et al., "Effectiveness of a Locking Plate in Preserving Midcalcaneal Length and Positional Outcome after vans Calcaneal Osteotomy: A Retrospective Pilot Study," The Journal of Foot and Ankle Surgery, vol. 52, 2013, pp. 710-713.

Dayton et al., "Principles of Management of Growth Plate Fractures in the Foot and Ankle," Clinics in Podiatric Medicine and Surgery, Pediatric Foot Deformities, Oct. 2013, 17 pages.

DeCarbo et al., "Resurfacing Interpositional Arthroplasty for Degenerative Joint Disease of the First Metatarsalphalangeal Joint," Podiatry Management, Jan. 2013, pp. 137-142.

Sandhu et al., "Digital Arthrodesis With a One-Piece Memory Nitinol Intrarnedullary Fixation Device: A Retrospective Review," Foot and Ankle Specialist, vol. 6, No. 5, Oct. 2013, pp. 364-366.

Catanese et al., "Measuring Sesarnoid Position in Hallux Valgus: When Is the Sesarnoid Axial View Necessary," foot and Ankle Specialist, 2014, 3 pages.

Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.

Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.

Dayton et al., "Clarification of the Anatomic Definition of the Bunion Deformity," The Journal of Foot and Ankle Surgery, vol. 53, 2014, pp. 160-163.

Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.

Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.

Dayton et al., "Observed Changes in Radiographic Measurements of the First Ray after Frontal and Transverse Plane Rotation of the

(56) References Cited

OTHER PUBLICATIONS

Hallux: Does the Hallux Drive the Metatarsal in a Bunion Deformity?," The Journal of Foot and Ankle Surgery, Article in Press, 2014, 4 pages.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Dayton et al., "Technique for Minimally Invasive Reduction of Calcaneal Fractures Using Small Bilateral External Fixation," The Journal of Foot and Ankle Surgery, Article in Press, 2014, 7 pages.
DeCarbo et al., "Locking Plates: Do They Prevent Complications?," Podiatry Today, Apr. 2014, 7 pages.
DeCarbo et al., "The Weil Osteotomy: A Refresher," Techniques in Foot and Ankle Surgery, vol. 13, No. 4, Dec. 2014, pp. 191-198.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Groves, "Operative Report," St. Tanunany Parish Hospital, Date of Procedure, Mar. 26, 2014, 2 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "Complications of Metatarsal Suture Techniques for Bunion Correction: A Systematic Review of the literature," The Journal of Foot and Ankle Surgery, Article in Press, 2015, 3 pages.
Defendant Fusion Orthopedics LLC's Invalidity Contentions, No. CV-22-00490-PHX-SRB, US District Court for the District of Arizona, Aug. 27, 2022, 41 pages.
Prior Art Publications, Exhibit A of Defendant Fusion Orthopedics LLC's Invalidity Contentions, No. CV-22-00490-PHX-SRB, US District Court for the District of Arizona, Aug. 27, 2022, 3 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 pages.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-2200490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490-PHX-SRB, US District Court for the District of Arizona, Aug. 27, 2022, 155 pages.
Hardy et al., "Observations on Hallux Valgus," The Journal of Bone and Joint Surgery, vol. 33B, No. 3, Aug. 1951, pp. 376-391.
Carr et al., "Correctional Osteotomy for Metatarsus Primus Varus and Hallux Valgus," The Journal of Bone and Joint Surgery, vol. 50-A, No. 7, Oct. 1968, pp. 1353-1367.
Alvine et al., "Peg and Dowel Fusion of the Proximal Interphalangeal Joint," Foot & Ankle, vol. 1, No. 2, 1980, pp. 90-94.
Dayton et al., "Biwinged Excision for Round Pedal Lesions," The Journal of Foot and Ankle Surgery, vol. 35, No. 3, 1996, pp. 244-249.
Myerson, "Cuneiform-Metatarsal Arthrodesis," The Foot and Ankle, Chapter 9, 1997, pp. 107-117.
Coughlin, "Fixation of the Lapidus Arthrodesis with a Plantar Interfragmentary Screw and Medial Low Profile locking Plate," Orthopaedics and Traumatology, vol. 7, 1999, pp. 133-143.
Bednarz et al., "Modified Lapidus Procedure for the Treatment of Hypermobile Hallux Valgus," Foot & Ankle International, vol. 21, No. 10, Oct. 2000, pp. 816-821.
Blomer, "Knieendoprothetik-Herstellerische Probleme und technologische Entwicklungen," Orthopade, vol. 29, 2000, pp. 688-696, including English Abstract on p. 689.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Schon et al., "Cuneiform-Metatarsal Arthrodesis for Hallux Valgus,"The Foot and Ankle, Second Edition, Chapter 8, 2002, pp. 99-117.
Sokoloff, "Lapidus Procedure," Textbook of Bunion Surgery, Chapter 15, 1981, pp. 277-287.
Dayton et al., "Use of the Z Osteotomy for Tailor Bunionectomy," The Journal of Foot and Ankle Surgery, vol. 42, No. 3, May/Jun. 2003, pp. 167-169.
Anderson et al., "Uncemented STAR Total Ankle Prostheses," The Journal of Bone and Joint Surgery, vol. 86(1, Suppl 2), Sep. 2004, pp. 103-111, (Abstract Only).
Dayton et al., "Early WeightbearingAfter First Metatarsophalangeal Joint Arthrodesis: A Retrospective Observational Case Analysis," The Journal of Foot and Ankle Surgery, vol. 43, No. 3, May/Jun. 2004, pp. 156-159.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Wukich et al., "Hypermobility of the First Tarsometatarsal Joint," Foot and Ankle Clinics, vol. 10, No. 1, Mar. 2005, pp. 157-166.
Baravarian, "Why the Lapidus Procedure is Ideal for Bunions," Podiatry Today, Retrieved online from <https://www.hmpglobal-learhmpgloballe.com/site/podipodi/article/5542>, dated May 2006, 8 pages.
Greiner, "The Jargon of Pedal Movements," Foot & Ankle International, vol. 28, No. 1, Jan. 2007, pp. 109-125.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Sanunarco, "Surgical Strategies: Mau Osteotomy for Correction of Moderate and Severe Hallux Valgus Deformity," Foot & Ankle International, vol. 28, No. 7, Jul. 2007, pp. 857-864.
Gerard et al., "The Modified Lapidus Procedure," Orthopedics, vol. 31, No. 3, Mar. 2008, 7 pages.
"Lapidus Pearls: Gaining Joint Exposure to Decrease Non-Union," Youtube, Retrieved online from <https://www.youtube.com/watch?vjqJyE7pj-Y>, dated Nov. 2, 2009, 3 pages.
"Visionaire: Patient Matched Cutting Blocks Surgical Procedure," Smith & Nephew, Inc., 2009, 2 pages.
Mote et al., "First Metatarsal-Cuneiform Arthrodesis for the Treatment of First Ray Pathology: A Technical Guide," JFAS Techniques Guide, vol. 48, No. 5, Sep./Oct. 2009, pp. 593-601.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Stamatis et al., "Mini Locking Plate as "Medial Buttress" for Oblique Osteotomy for Hallux Valgus," Foot & Ankle International, vol. 31, No. 10, Oct. 2010, pp. 920-922.

(56) References Cited

OTHER PUBLICATIONS

Bouaicha et al., "Fixation of Maximal Shift Scarf Osteotomy with Inside Out Plating: Technique Tip," Foot & Ankle International, vol. 32, No. 5, May 2011, pp. 567-569.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Albano et al., "Biomechanical Study of Transcortical or Transtrabecular Bone Fixation of Patellar Tendon Graft with Bioabsorbable Pins in ACL Reconstruction in Sheep," Revista Brasileira de Ortopedia (Rev Bras Ortop.) vol. 47, No. 1, 2012, pp. 43-49.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Giannoudis et al., "Hallux Valgus Correction," Practical Procedures in Elective Orthopaedic Surgery, Pelvis and Lower Extremity, Chapter 38, 2012, 22 pages.
Holmes, Jr., "Correction of the Intermetatarsal Angle Component of Hallux Valgus Using Fiberwire-Attached Endo-buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
"Foot and Ankle Instrument Set," Smith & Nephew, 2013, 2 pages.
Arthrex, "Comprehensive Foot System," Retrieved online from <https://www.arthrex.com/resources/animation/8U3iaPvY6k0 8bwFAwZF 50Q/comprehensivefootsystem?referringTeamfoot_and_ankle>, dated Aug. 27, 2013, 3 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Didomenico et al., "Lapidus Bunionectomy: First Metatarsal Cuneiform Arthrodesis," McGlamry's Comprehensive Textbook of Foot and Ankle Surgery, Fourth Edition, vol. 1, Chapter 31, 2013, 24 pages.
Fishco, "A Straightforward Guide To The Lapidus Bunionectomy,"Podiatry Today, Retrieved online from <https://www.hmpgloballeamingnetwork.com/site/podiatry/blogged/straightforwardguide-lapidus-bunionectomy>, dated Sep. 6, 2013, 5 pages.
"Acumed Osteotomiesystem Operationstechnik," Acumed, 2014, 19 pages (including 3 pages English translation).
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Fishco, "Making the Lapidus Easy," The Podiatry Institute, Update 2014, Chapter 14, 2014, pp. 91-93.
Fallin et al., US Provisional Application Entitled Indexed Tri-Planar Osteotomy Guide and Method, U.S. Appl. No. 62/118,378, filed Feb. 19, 2015, 62 pages.
Groves, "Functional Position Joint Sectioning: Pre-Load Method for Lapidus Arthrodesis," The Podiatry Institute, Update 2015, Chapter 6, 2015, pp. 23-29.
Reconstructive Surgery of the Foot & Ankle, The Podiatry Institute, Update 2015, Conference Program, May 2015, 28 pages.
"Accu-Cut Osteotomy Guide System," BioPro, Brochure, Oct. 2018, 2 pages.
Obviousness Chart, Exhibit C of Defendant Fusion Orthopedics LLC's Invalidity Contentions, No. CV-22-00490-PHX-SRB, US District Court for the District of Arizona, Aug. 27, 2022, 153 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX-SRB, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit BS of Defendant Fusion Orthopedics LLC's Invalidity Contentions, No. CV-22-00490-PHX-SRB, US District Court for the District of Arizona, Aug. 27, 2022, 110 pages.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Coetzee et al., "The Lapidus Procedure: A Prospective Cohort Outcome Study," Foot & Ankle International, vol. 25, No. 8, Aug. 2004, pp. 526-531.
Lapidus, "The Author's Bunion Operation From 1931 to 1959," Clinical Orthopaedics, vol. 16, 1960, pp. 119-135.
Gotte, "Entwicklung eines Assistenzrobotersystems fiir die Knieendoprothetik," Forschungsberichte, Technische Universitat Munchen, 165, 2002, 11 pages, including partial English Translation.
"Lag Screw Target Bow," Stryker Leibinger GmbH & Co. KG, Germany 2004, 8 pages.
Grondal et al., "A Guide Plate for Accurate Positioning of First Metatarsophalangeal Joint during Fusion," Operative Orthopiidie Und Traumatologie, vol. 16, No. 2, 2004, pp. 167-178 (Abstract Only).
Garthwait, "Accu-Cut System Facilitates Enhanced Precision," Podiatry Today, vol. 18, No. 6, Jun. 2005, 6 pages.
"Hoffmann II Compact External Fixation System," Stryker, Brochure, Literature No. 5075-1-500, 2006, 12 pages.
Smith & Nephew, Inc, "Proximal Humerus Locking Plate," PeriLoe Upper Extremity Locked Plating System, Surgical Technique, Sep. 2006, 36 pages.
Gregg et al., "Plantar plate repair and Weil osteotomy for metatarsophalangeal joint instability," Foot and Ankle Surgery, vol. 13, 2007, pp. 116-121.
"Futura Forefoot Implant Arthroplasty Products," Tornier, Inc., 2008, 14 pages.
"Hoffmann II Micro Lengthener," Stryker, Operative Technique, Literature No. 5075-2-002, 2008, 12 pages.
Hetherington et al., "Evaluation of surgical experience and the use of an osteotomy guide on the apical angle of an Austin osteotomy," The Foot, vol. 18, 2008, pp. 159-164.
Stryker, "VariAx Foot Locked Plating System," Jun. 2008, 25 pages.
Monnich et al., "A Hand Guided Robotic Planning System for Laser Osteotomy in Surgery," World Congress on Medical Physics and Biomedical Engineering vol. 25/6: Surgery, Minimal Invasive Interventions, Endoscopy and Image Guided Therapy, Sep. 7-12, 2009, pp. 59-62, (Abstract Only).
Synthes, "LCP Periprosthetic System," 2009, 8 pages.
Magin, "Computernavigierter Gelenkersatz am Knie mit dem Orthopilot," Operative Orthopiidie und Traumatologie, vol. 22, No. 1, 2010, pp. 63-80, including English Abstract on p. 64.
MiniRail System, Small Bone Innovations, Surgical Technique, 2010, 24 pages.
Moore et al., "Effect of Ankle Flexion Angle on Axial Alignment of Total Ankle Replacement," Foot and Ankle International, vol. 31, No. 12, Dec. 2010, pp. 1093-1098, (Abstract Only).
Rochet et al., "Proximal Ulna Comminuted Fractures: Fixation Using a Double-Plating Technique," Revue de Chirurgie Orthopedique et Traumatologique, vol. 96, No. 7, Nov. 2010, pp. 800-807.
Gonzalez Del Pino et al., "Variable Angle Locking Intercarpal Fusion System for Four-Corner Arthrodesis: Indications and Surgical Technique," Journal of Wrist Surgery, vol. 1, No. 1, Aug. 2012, pp. 73-78.
Miyake et al., "Three-Dimensional Corrective Osteotomy for Malunited Diaphyseal Forearm Fractures Using Custom-Made Surgical Guides Based on Computer Simulation," JBJS Essential Surgical Techniques, vol. 2, No. 4, 2012, 11 pages.
Mortier et al., "Axial Rotation of the First Metatarsal Head in a Normal Population and Hallux Valgus Patients," Orthopaedics and Traumatology: Surgery and Research, vol. 98, 2012, pp. 677-683.

(56) References Cited

OTHER PUBLICATIONS

Dobbe et al. "Patient-Tailored Plate for Bone Fixation and Accurate 3D Positioning in Corrective Osteotomy," Medical and Biological Engineering and Computing, vol. 51, No. 1-2, Feb. 2013, pp. 19-27, (Abstract Only).
Doty et al., "Hallux valgus and hypermobility of the first ray: facts and fiction," International Orthopaedics, vol. 37, 2013, pp. 1655-1660.
Modular Rail System: External Fixator, Smith & Nephew, Surgical Technique, 2013, 44 pages.
Smith & Nephew, Inc, "Medial Column Fusion for Midfoot Deformity Correction," VLP Foot Variable Angle Locked Plating System, Surgical Technique, 2013, 20 pages.
"HAT-TRICK Lesser Toe Repair System, Foot and Ankle Technique Guide, Metatarsal Shortening Osteotomy Surgical Technique," Smith & Nephew, 2014, 16 pages.
"HAT-TRICK Lesser Toe Repair System," Smith & Nephew, Brochure, Aug. 2014, 12 pages.
"Hoffmann Small System External Fixator Orthopedic Instruments," Stryker, retrieved Dec. 19, 2014, from the Internet: <http://www.alibaba.corn/product-detail/Stryker-Hoffmann-Srnall-SystemExternal-Fixator_I438850129.htrnl>, 3 pages.
Dayton et al., "Observed Changes in Radiographic Measurements of the First Ray after Frontal and Transverse Plane Rotation of the Hallux: Does the Hallux Drive the Metatarsal in a Bunion Deformity? ," The Journal of Foot and Ankle Surgery, vol. 53, 2014, pp. 584-587.
Didomenico et al., "Correction of Frontal Plane Rotation of Sesamoid Apparatus during the Lapidus Procedure: A Novel Approach," The Journal of Foot and Ankle Surgery, vol. 53, 2014, pp. 248-251.
EBI Extra Small Rail Fixator, Biomet Trauma, retrieved Dec. 19, 2014, from the Internet: <http://footandanklefixation.com/product/biomet-trauma-ebi-extra-small-rail-fixator>, 7 pages.
Hirao et al., "Computer assisted planning and custom-made surgical guide for malunited pronation deformity after first metatarsophalangeal joint arthrodesis in rheumatoid arthritis: A case report," Computer Aided Surgery, vol. 19, Nos. 1-3, 2014, pp. 13-19.
Lieske et al., "Implantation einer Sprunggelenktotalendo-prothese vom Typ Saito 2," Operative Orthopiidie und Traumatologie, vol. 26, No. 4, 2014, pp. 401-413, including English Abstract on p. 403.
MAC (Multi Axial Correction) Fixation System, Biomet Trauma, retrieved Dec. 19, 2014, from the Internet: <http://footandanklefixation.corn/product/biomet-trauma-mac-multi-axial-correction-fixation system>, 7 pages.
Magin, "Die belastungsstabile Lapidus-Arthrodese bei Halluxvalgus-Deformitiit mittels IVP-Plattenfixateur (V-TEK-System)," Operative Orthopiidie und Traumatologie, vol. 26, No. 2, 2014, pp. 184-195, including English Abstract on p. 186.
Mini Joint Distractor, Arthrex, retrieved Dec. 19, 2014, from the Internet: <http://www.arthrex.com/foot-ankle/mini-joint-distractor/products>, 2 pages.
Smith & Nephew, Inc, "D-RAD Smart Pack," Single-Use Volar Distal Radius Plating System, Brochure, Jun. 2014, 8 pages.
Dayton et al., "Is Our Current Paradigm for Evaluation and Management of the Bunion Deformity Flawed? A Discussion of Proce dure Philosophy Relative to Anatomy," The Journal of Foot and Ankle Surgery, vol. 54, 2015, pp. 102-111.
Dayton et al., "Quantitative Analysis of the Degree of Frontal Rotation Required to Anatomically Align the First Metatarsal Phalangeal Joint During Modified Tarsal-Metatarsal Arthrodesis Without Capsular Balancing," The Journal of Foot and Ankle Surgery, 2015, pp. 1-6.
De Geer et al., "A New Measure of Tibial Sesamoid Position in Hallux Valgus in Relation to the Coronal Rotation of the First Metatarsal in CT Scans," Foot and Ankle International, Mar. 26, 2015, 9 pages.
Galli et al., "Enhanced Lapidus Arthrodesis: Crossed Screw Technique With Middle Cuneiform Fixation Further Reduces Sagittal Mobility," The Journal of Foot & Ankle Surgery, vol. 54, vol. 3, May/Jun. 2015, published online: Nov. 21, 2014, pp. 437-440.
Kim et al., "A New Measure of Tibial Sesarnoid Position in Hallux Valgus in Relation to the Coronal Rotation of the First Metatarsal in CT Scans," Foot and Ankle International, vol. 36, No. 8, 2015, pp. 944-952.
Smith & Nephew, Inc, "Evos Mini," Plating System, Brochure, May 2015, 12 pages.
Stryker, "Anchorage Plating System," Operative Technique, Rev. 2, Aug. 2015, 32 pages.
Dayton et al., "Comparison of the Mechanical Characteristics of a Universal Small Biplane Plating Technique Without Compression Screw and Single Anatomic Plate With Compression Screw," The Journal of Foot & Ankle Surgery, vol. 55, No. 3, May/Jun. 2016, published online: Feb. 9, 2016, pp. 567-571.
Tornier, "CoverLoc Volar Plate," Retrieved from <http://www.tornier-us.com/upper/hand/writra003/>, 2016, 2 pages.
Tornier, "DFX Distal Fibula and DTX Distal Tibia Plates," Retrieved from <http://www.tornier-us.com/lower/ankle/anktra003/>, 2016, 2 pages.
Tornier, "Hand and Wrist," Retrieved from <http://www.tornier-us.com/upper/hand/>, 2016, 1 page.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot and Ankle Surgery, vol. 52, No. 3, May/Jun. 2013, pp. 348-354.
Michelangelo Bunion System, Surgical Technique, Instratek Inco** porated, publication date unknown, 4 pages.
Scranton Jr. et al., "Anatomic Variations in the First Ray: Part I. Anatomic Aspects Related to Bunion Surgery," Clinical Orthopaedics and Related Research, vol. 151, Sep. 1980, pp. 244-255.
Odenbring et al., "A guide instrument for high tibial osteotomy," Acta Orthopaedica Scandinavica, vol. 60, No. 4, 1989, pp. 449-451.
Horton et al., "Deformity Correction and Arthrodesis of the Midfoot with a Medial Plate," Foot & Ankle, vol. 14, No. 9, Nov./Dec. 1993, pp. 493-499.
Chang et al., "Lapidus Arthrodesis: A Different Perspective," Jour nal of the American Podiatric Medical Association, vol. 84, No. 6, Jun. 1994, pp. 281-288.
Talbot et al., "Assessing Sesamoid Subluxation: How Good is the AP Radiograph?," Foot and Ankle International, vol. 19, No. 8, Aug. 1998, pp. 547-554.
"Patient to Patient Precision, Accu-Cut, Osteotomy Guide System," BioPro, Foot & Ankle International Journal, vol. 23, No. 8, Aug. 2002, 2 pages.
Wendi et al., "Navigation in der Knieendoprothetik," OP-Journal, vol. 17, 2002, pp. 22-27, including English Abstract.
Whipple et al., "Zimmer Herbert Whipple Bone Screw System: Surgical Techniques for Fixation Of Scaphoid and Other Small Bone Fractures," Zimmer, 2003, 59 pages.
Patel et al., "Modified Lapidus Arthrodesis: Rate of Nonunion in 227 Cases," The Journal of Foot & Ankle Surgery, vol. 43, No. 1, Jan./Feb. 2004, pp. 37-42.
Weber et al., "A Simple System for Navigation of Bone Alignment Osteotomies of the Tibia," International Congress Series, vol. 1268, Jan. 2004, pp. 608-613, (Abstract Only).
Stahl et al., "Derotation of Post-Traumatic Femoral Deformities by Closed Intramedullary Sawing," Injury, vol. 37, No. 2, Feb. 2006, pp. 145-151, (Abstract Only).
NexFix from Nexa Orthopedics, MetaFix I from Merete Medical, Inc. and The BioPro Lower Extremities from BioPro, found in Foot & Ankle International Journal, vol. 28, No. 1, Jan. 2007, 4 pages.
Toth et al., "The Effect of First Ray Shortening in the Development of Metatarsalgia in the Second Through Fourth Rays After Meta tarsal Osteotomy," Foot & Ankle International, vol. 28, No. 1, Jan. 2007, pp. 61-63.
Simpson et al., "Computer-Assisted Distraction Ostegogenesis by Ilizarov's Method," International Journal of Medical Robots and Computer Assisted Surgery, vol. 4, No. 4, Dec. 2008, pp. 310-320, (Abstract Only).
Vitek et al., "Die Behandlung des Hallux rigidus mit Cheilektomie und Akin-Moberg-Osteotomie unter Verwendung einer neuen Schnit-

(56) References Cited

OTHER PUBLICATIONS tlehre und eines neuen Schraubensystems," Orthopadische Praxis, vol. 44, Nov. 2008, pp. 663-566, including English Abstract on p. 564.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Okuda et al., "Postoperative Incomplete Reduction of the Sesamoids as a Risk Factor for Recurrence of Hallux Valgus," The Journal of Bone and Joint Surgery, vol. 91-A, No. 1, Jul. 2009, pp. 1637-1645.
Plaass et al., "Anterior Double Plating for Rigid Fixation of Isolated Tibiotalar Arthrodesis," Foot and Ankle International, vol. 30, No. 7, Jul. 2009, pp. 631-639.
Saltzman et al., "Prospective Controlled Trial of STAR Total Ankle Replacement Versus Ankle Fusion: Initial Results," Foot & Ankle International, vol. 30, No. 7, Jul. 2009, pp. 579-596.
Vitek, "Neue Techniken in der FuBchirurgie Das V-tek-System," ABW Wissenschaftsverlag GmbH, 2009, 11 pages, Including English Abstract.
Scanlan et al. "Technique Tip: Subtalar Joint Fusion Using a Parallel Guide and Double Screw Fixation," The Journal of Foot and Ankle Surgery, vol. 49, Issue 3, May-Jun. 2010, pp. 305-309, (Abstract Only).
Yakacki et al. "Compression Forces of Internal and External Ankle Fixation Devices with Simulated Bone Resorption," Foot and Ankle International, vol. 31, No. 1, Jan. 2010, pp. 76-85, (Abstract Only).
Weil et al., "Anatomic Plantar Plate Repair Using the Weil Metatarsal Osteotomy Approach," Foot & Ankle Specialist, vol. 4, No. 3, 2011, pp. 145-150.
Acumed, "Acu-Loc Wrist Plating System," Brochure and Surgical Technique, effective date Apr. 2012, reported publication date Sep. 23, 2013, 19 pages.
TempFix Spanning the Ankle Joint Half Pin and Transfixing Pin Techniques, Biomet Orthopedics, Surgical Technique, 2012, 16 pages.
Tricot et al., "3D-corrective osteotomy using surgical guides for posttraumatic distal humeral deformity," Acta Orthopaedica Belgica, vol. 78, No. 4, 2012, pp. 538-542.
"Prophecy In bone Preoperative Navigation Guides," Wright Medical Technology, Inc., Nov. 2013, 6 pages.
"RAYHACK Ulnar Shortening Generation II Low-Profile Locking System Surgical Technique," Wright Medical Technology, Inc., Dec. 2013, 20 pages.
Otsuki et al., "Developing a novel custom cutting guide for curved per-acetabular osteotomy," International Orthopaedics (SICOT), vol. 37, 2013, pp. 1033-1038.
Peters et al., "Flexor Hallucis Longus Tendon Laceration as a Complication of Total Ankle Arthroplasty," Foot & Ankle International, vol. 34, No. 1, 2013, pp. 148-149.
Siddiqui et al. "Fixation of Metatarsal Fracture With Bone Plate in a Dromedary Heifer," Open Veterinary Journal, vol. 3, No. 1, 2013, pp. 17-20.
Sidekick Stealth Rearfoot Fixator, Wright Medical Technology, Surgical Technique, Dec. 2, 2013, 20 pages.
"Smith & Nephew scores a HAT-TRICK with its entry into the high-growth hammer toe repair market," Smith & Nephew, Jul. 31, 2014, 2 pages.
Acumed, "Hand Fracture System," Brochure, effective date Sep. 2014, reported publication date Jan. 29, 2016, 6 pages.
Couzens et al., "Stainless Steel Versus Titanium Volar Multi-Axial Locking Plates for Fixation of Distal Radius Fractures: A Randomised Clinical Trial," BMC Musculoskeletal Disorders, vol. 15, No. 74, Mar. 2014, 7 pages.
Osher et al., "Accurate Determination of Relative Metatarsal Protrusion with a Small Intermetatarsal Angle: A Novel Simplified Method," The Journal of Foot & Ankle Surgery, vol. 53, No. 5, Sep./Oct. 2014, published online: Jun. 3, 2014, pp. 548-556.
Osteomed, "ExtremiLock Ankle Plating System," Brochure, published prior to Nov. 20, 2014, 6 pages.
Osteomed, "ExtremiLock Foot Plating System," Brochure, published prior to Nov. 20, 2014, 6 pages.
Osteomed, "Hand Plating System," Brochure, published prior to Nov. 20, 2014, 8 pages.
Rx-Fix Mini Rail External Fixator, Wright Medical Technology, Brochure, Aug. 15, 2014, 2 pages.
Small Bone External Fixation System, Acumed, Surgical Technique, Effective date Sep. 2014, 8 pages.
Arthrex, "Plantar Lapidus Plate," 2015, 6 pages.
Stableloc External Fixation System, Acumed, Product Overview, Effective date Sep. 2015, 4 pages.
Yasuda et al., "Proximal Supination Osteotomy of the First Metatarsal for Hallux Valgus," Foot and Ankle International, vol. 36, No. 6, Jun. 2015, pp. 696-704.
Acumed, "Hub Cap Fusion Plates," Retrieved from <http://www.acumed.net/products/hand-wrist/carpal/hub-cap-fusion-plates>, 2016, 8 pages.
Arthrex, "Double Compression Plates," Retrieved from <https://www.arthrex.com/foot-ankle/double-compression-plates>, 2016, 3 pages.
Arthrex, "Proximal Metatarsal Osteotomy using Plates," Retrieved from <http://www.arthrex.com/foot-ankle/proximal-metatarsal osteotomy-using-plates>, 2016, 2 pages.
Merete GMBH, "MetaFix OpenWedge," Retrieved from <http://www.merete-medical.com/de/produkte/fuss/hallux-valgus/metafixropenwedge.htrnl>, 2016, 4 pages (Google Translation).
Plaass et al., "Placement of Plantar Plates for Lapidus Arthrodesis: Anatomical Considerations," Foot and Ankle International, vol. 37, No. 4, Apr. 2016, pp. 427-432.
Diaconu et al., "Locking Plates for Fixation of Extra-Articular Fractures of the First Metacarpal Base: A Series of 15 Cases," Chirurgie de la Main, vol. 30, No. 1, pp. 26-30, Abstract only.

* cited by examiner

MULTI-DIAMETER K-WIRE FOR ORTHOPEDIC APPLICATIONS

RELATED MATTERS

This application is a continuation of U.S. patent application Ser. No. 17/018,422, filed Sep. 11, 2020, which claims the benefit of U.S. Provisional Application No. 62/900,391, filed Sep. 13, 2019. The entire contents of each of these applications are incorporated herein by reference.

TECHNICAL FIELD

This disclosure relates to orthopedic devices and techniques.

BACKGROUND

Kirschner wires, or K-wires, are sterilized, sharpened, smooth or threaded metal pins configured for a variety of medical, orthopedic, dental, and plastic surgical procedures, as well as various types of veterinary surgeries. K-wires can be used to hold bone fragments together and/or to provide an anchor for skeletal traction. A K-wire may be driven into bone using a powered or hand drill.

Example applications in which K-wires may be used include procedures for realigning comparatively small bones within in the human body, such as bones in the hand or foot. These bones may be misaligned and require anatomical realignment with the aid of a K-wire during a surgical procedure. For example, one common type of bone deformity is hallux valgus, which is a progressive foot deformity in which the first metatarsophalangeal joint is affected and is often accompanied by significant functional disability and foot pain. The metatarsophalangeal joint is laterally deviated, resulting in an abduction of the first metatarsal while the phalanges adduct. This often leads to development of soft tissue and a bony prominence on the medial side of the foot, which is called a bunion. Surgical intervention may be used to correct a bunion deformity.

SUMMARY

In general, this disclosure is directed to multi-diameter fixation pins for orthopedic procedures, such as multi-diameters K-wires, and techniques utilizing such a fixation pin. A multi-diameter fixation pin can be inserted into a bone during an orthopedic procedure, such as inserted through one bone portion into an adjacent bone portion to fixate the two bone portions relative to each other. The two bone portions may be different portions of the same bone (e.g., separated by a cut or fracture) or different two different bones. In either case, a multi-diameter fixation pin according to the disclosure may include a leading diameter sized for the specific orthopedic procedure being undertaken and/or the size of the bone into which the fixation pin is being inserted. The multi-diameter fixation pin may also include a trailing diameter different than the leading diameter. The trailing diameter may be sized for use with a specific sized powered driver. For example, in orthopedic procedures that involve inserting larger diameter pins and smaller diameter pins into bone(s), all pins used in the procedure may have a trailing diameter (e.g., the larger diameter or the smaller diameter) that allows the pins to be inserted with the same powered driver (e.g., the same attachment head) without needing different sized drivers or attachment heads for different sized pins.

As an example implementation, a clinician may select a powered driver and/or a collet for the powered driver that is configured to receive a certain size fixation pin or certain range of sizes of fixation pins. For example, the clinician may from select one collet for the powered driver from a set of different collets, each of which is sized to receive a different size fixation pin (or range of sizes). The clinician can insert the selected collet into the powered driver. The clinician can then use the powered driver with selected collet to insert multiple fixation pins into one or more bone portions during a procedure.

The clinician can insert a fixation pin having a size acceptable for use with the selected collet into the powered driver and then use the powered driver to drive the fixation pin into one or more bone portions. The fixation pin can have a constant (e.g., same) diameter over it length, e.g., optionally with narrowing or other shaping features adjacent the tip. Before or after inserting the fixation pin with constant diameter into the powered driver and then into a bone portion, the clinician may also wish to insert a fixation pin into a bone portion having a diameter outside of the size acceptable for use with the selected collet. Traditionally, this would require the clinician to obtain a different powered driver or change the collet on the powered driver, necessitating additional time and procedural steps.

A multi-diameter fixation pin according to some examples of the present disclosure can be configured with a driver engagement portion and a bone insertion portion. The driver engagement portion can have a diameter different (smaller or larger) than the bone insertion portion. The driver engagement portion may have a size corresponding to the size of one or more other constant diameter fixation pins used during the surgical procedure. The driver engagement portion of the multi-diameter fixation pin can have a size acceptable for use with the selected collet of the powered driver that is appropriately sized for receiving and driving one or more other constant diameter fixation pins. However, the bone insertion portion of the multi-diameter fixation pin can have a different diameter. As a result, the clinician can insert the multi-diameter fixation pin into the powered driver without changing drivers and/or collets used for inserting one or more other fixation pins during the procedure and insert a portion of the multi-diameter fixation pin into one or more bone portions that has a size not otherwise acceptable for use with the collet and/or driver.

In one example, a method is described that includes inserting a pin having a first diameter into a collet of a powered driver and driving the pin into at least one of a metatarsal and a cuneiform. The method further involves moving the metatarsal relative to the cuneiform to establish a moved position of the metatarsal. The method also includes inserting a driver engagement portion of a multi-diameter fixation pin into the collet of the driver and driving a bone insertion portion of the multi-diameter fixation pin through the metatarsal and into another bone to hold the moved position of the metatarsal. The example specifies that the collet of the powered driver is sized to receive the pin having the first diameter and the driver engagement portion of the multi-diameter fixation pin but not the bone insertion portion of the multi-diameter fixation pin.

In another example, a method is described that includes inserting a driver engagement portion of a multi-diameter fixation pin into a collet of a powered driver and driving a bone insertion portion of the multi-diameter fixation pin through one or more bone portions. The example specifies that the collet of the powered driver is sized to receive the driver engagement portion of the multi-diameter fixation pin but not the bone insertion portion of the multi-diameter fixation pin.

In another example, a surgical fixation wire is described. The surgical fixation wire has a body extending from a first end to a second end opposite the first end. The body defines a driver engagement portion having a first diameter and a bone insertion portion having a second diameter less than the first diameter. The example specifies that the first end of the body defines a tip configured for insertion into a bone and the driver engagement portion is configured for insertion into a powered driver.

The details of one or more examples are set forth in the accompanying drawings and the description below. Other features, objects, and advantages will be apparent from the description and drawings, and from the claims.

DETAILED DESCRIPTION

Figure 1A:
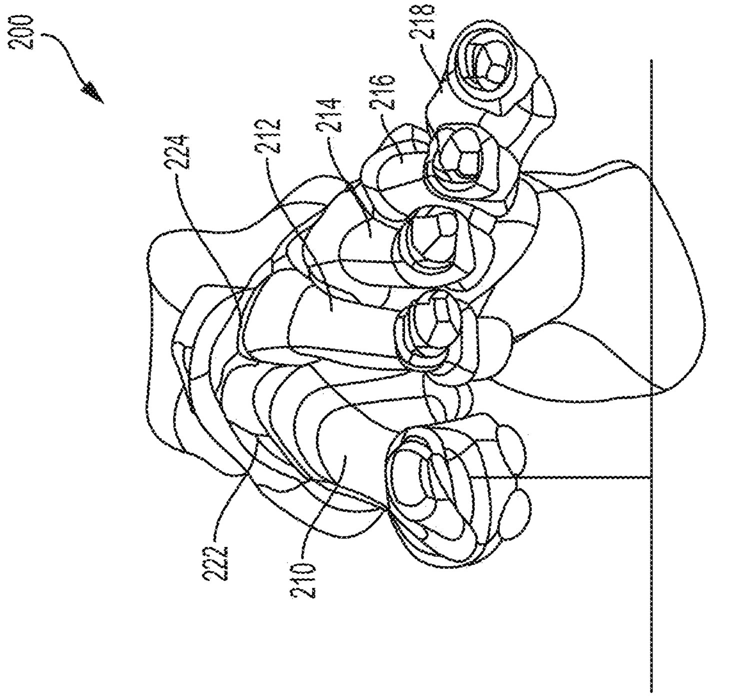
FIGS. 1A and 1B are front views of a foot showing a normal first metatarsal position and an example frontal plane rotational misalignment position, respectively.

In general, this disclosure is directed to fixation pins used during orthopedic procedures and techniques utilizing such fixation pins. As used herein, the terms “fixation pin” and “fixation wire” are generally used interchangeably. In practice, clinicians may generally refer to fixation pins having a comparatively small diameter (e.g., 1.6 mm or less) as a fixation wire and fixation pins having a comparatively larger diameter is just a fixation pin. However, the specific nomenclature choice between pin and wire can vary between clinicians and providers. Accordingly, multi-diameter fixation pins as described herein can also embrace multi-diameter fixation wires. Example embodiments of the fixation pins include multi-diameter Kirschner wires, or K-wires, and multi-diameter Steinmann pins.

A multi-diameter fixation pin as described herein can be used in any desired orthopedic procedure, including procedures utilizing only a single fixation pin or procedures utilizing multiple fixation pins (which may all be multi-diameter fixation pins as described herein or a combination of multi-diameter fixation pins and constant diameter fixation pins). The multi-diameter fixation pin can be inserted into a single bone portion or into multiple bone portions when used during the orthopedic procedure. For example, the multi-diameter fixation pin may be inserted through one bone portion and into an adjacent bone portion. The two bone portions may be different portions of the same bone (e.g., separated by a cut or fracture). Alternatively, the two bone portions may be different bones, such as to adjacent bones separated by a joint space.

In an example implementation, a multi-diameter fixation pin can be used during a surgical joint realignment procedure. For example, a multi-diameter fixation pin can be used during a surgical procedure, such as a bone alignment, osteotomy, fusion procedure, and/or other procedures where one or more bones are to be prepared (e.g., cartilage or bone removal and/or cut). Such a procedure can be performed, for example, on bones (e.g., adjacent bones separated by a joint or different portions of a single bone) in the foot or hand, where bones are relatively smaller compared to bones in other parts of the human anatomy. In one example, a procedure utilizing a multi-diameter fixation pin can be performed to correct an alignment between a metatarsal (e.g., a first metatarsal) and a second metatarsal and/or a cuneiform (e.g., a medial, or first, cuneiform), such as in a bunion correction surgery. An example of such a procedure is a Lapidus procedure (also known as a first tarsal-metatarsal fusion). In another example, the procedure can be performed by modifying an alignment of a metatarsal (e.g., a first metatarsal). An example of such a procedure is a basilar metatarsal osteotomy procedure.

A multi-diameter fixation pin may be used with one or more other instruments, such as a bone positioning guide and/or a bone preparation guide. The bone preparation guide may be pinned by one or more fixation pins to one or more bone portions to facilitate preparation of adjacent bone portions for fusion. The bone positioning guide may be used to impart a force to one bone portion to move the bone portion relative to another bone portion.

In some examples, one or more multi-diameter fixation pins are used during a realignment procedure in which a metatarsal (e.g., first metatarsal) is moved relative to and oppose cuneiform across a tarsal-metatarsal joint to establish a moved position of the metatarsal. One or more constant diameter fixation pins (fixation pins not having a multiple diameter) may be used during the surgical procedure. The constant diameter fixation pin(s) may have a diameter different (e.g., smaller or larger) than the diameter of the bone insertion portion of the multi-diameter fixation pin. Accordingly, use of the multi-diameter fixation pin can allow the clinician to insert a fixation pin having a different diameter than the constant diameter fixation pins into one or more bone portions during the surgical procedure without changing driver hardware.

Figure 1B:
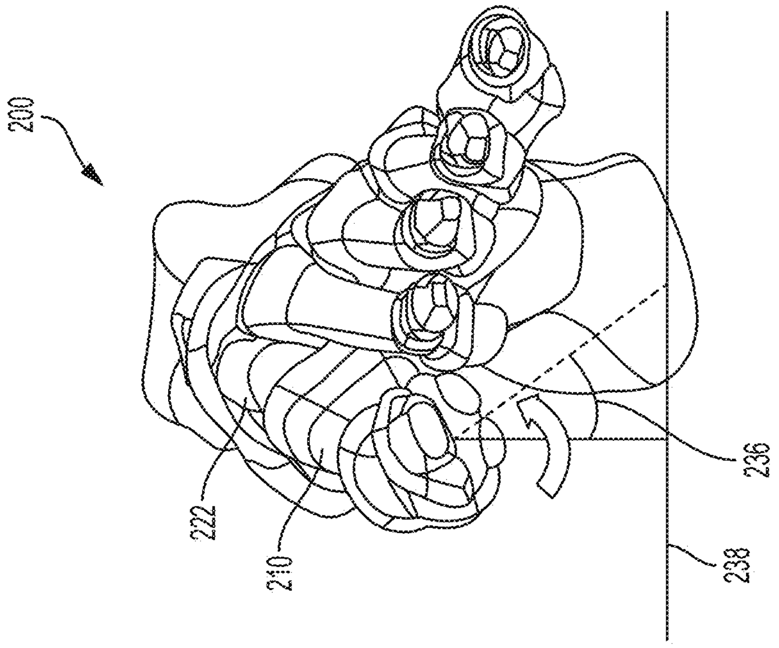
Figure 2B:
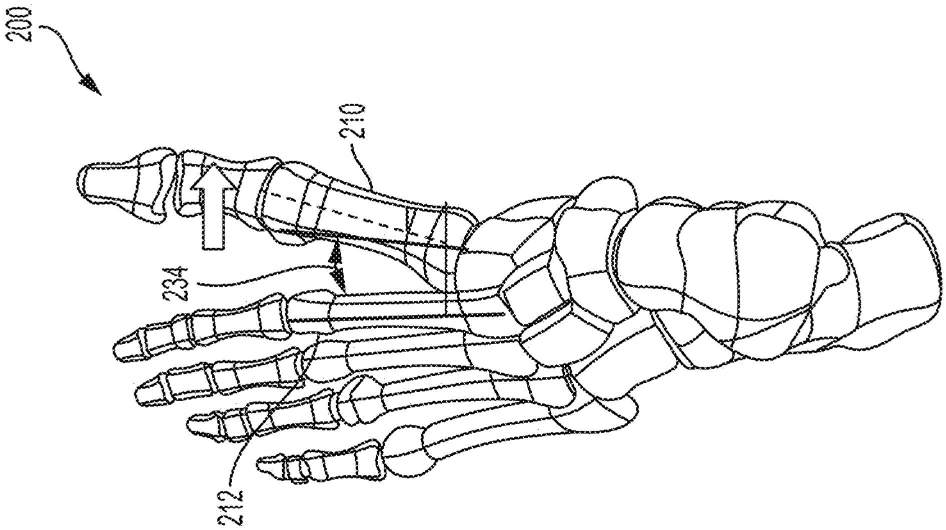
FIGS. 2A and 2B are top views of a foot showing a normal first metatarsal position and an example transverse plane misalignment position, respectively.
Figure 2A:
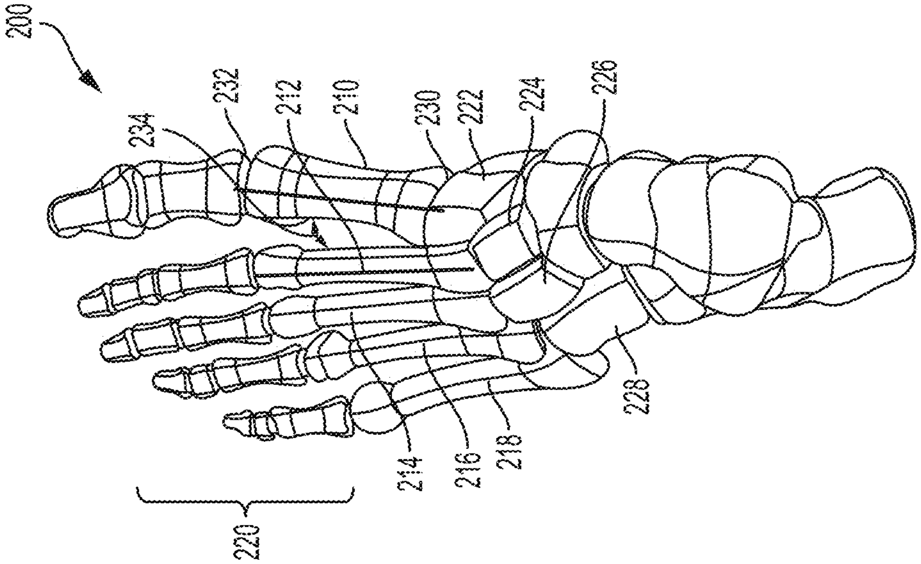
Figure 3B:
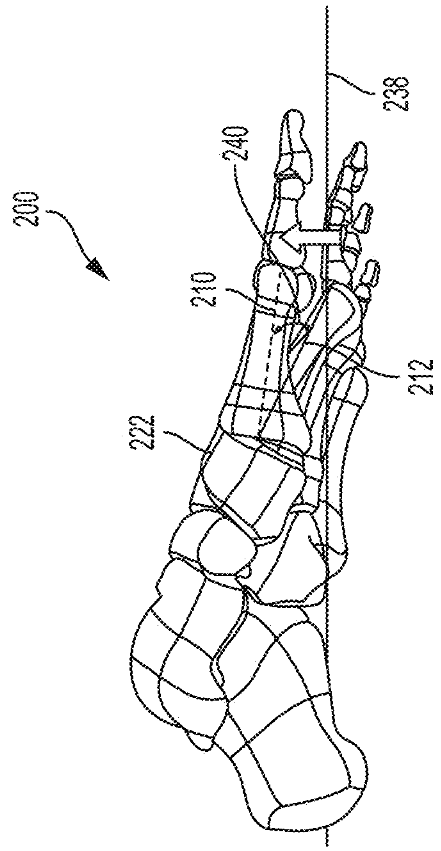
FIGS. 3A and 3B are side views of a foot showing a normal first metatarsal position and an example sagittal plane misalignment position, respectively.
Figure 3A:
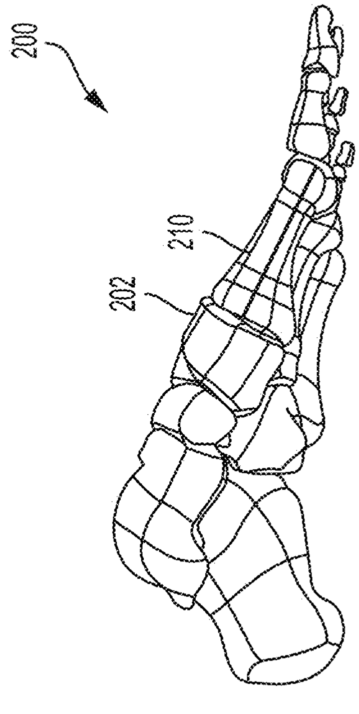

FIGS. 1-3 are different views of a foot 200 showing example anatomical misalignments that may occur and be corrected according to the present disclosure. Such misalignment may be caused by a hallux valgus (bunion), natural growth deformity, or other condition causing anatomical misalignment. FIGS. 1A and 1B are front views of foot 200 showing a normal first metatarsal position and an example frontal plane rotational misalignment position, respectively. FIGS. 2A and 2B are top views of foot 200 showing a normal first metatarsal position and an example transverse plane misalignment position, respectively. FIGS. 3A and 3B are side views of foot 200 showing a normal first metatarsal position and an example sagittal plane misalignment position, respectively. While FIGS. 1B, 2B, and 3B show each respective planar misalignment in isolation, in practice, a metatarsal may be misaligned in any two of the three planes or even all three planes. Accordingly, it should be appreciated that the depiction of a single plane misalignment in each of FIGS. 1B, 2B, and 3B is for purposes of illustration and a metatarsal may be misaligned in multiple planes that is desirably corrected.

With reference to FIGS. 1A and 2A, foot 200 is composed of multiple bones including a first metatarsal 210, a second metatarsal 212, a third metatarsal 214, a fourth metatarsal 216, and a fifth metatarsal 218. The metatarsals are connected distally to phalanges 220 and, more particularly, each to a respective proximal phalanx. The first metatarsal 210 is connected proximally to a medial cuneiform 222, while the second metatarsal 212 is connected proximally to an intermediate cuneiform 224 and the third metatarsal is connected proximally to lateral cuneiform 226. The fourth and fifth metatarsals 216, 218 are connected proximally to the cuboid bone 228. The joint 230 between a metatarsal and respective cuneiform (e.g., first metatarsal 210 and medial cuneiform 222) is referred to as the tarsometatarsal ("TMT") joint. The joint 232 between a metatarsal and respective proximal phalanx is referred to as a metatarsophalangeal joint. The angle 234 between adjacent metatarsals (e.g., first metatarsal 210 and second metatarsal 212) is referred to as the intermetatarsal angle ("IMA").

As noted, FIG. 1A is a frontal plane view of foot 200 showing a typical position for first metatarsal 210. The frontal plane, which is also known as the coronal plane, is generally considered any vertical plane that divides the body into anterior and posterior sections. On foot 200, the frontal plane is a plane that extends vertically and is perpendicular to an axis extending proximally to distally along the length of the foot. FIG. 1A shows first metatarsal 210 in a typical rotational position in the frontal plane. FIG. 1B shows first metatarsal 210 with a frontal plane rotational deformity characterized by a rotational angle 236 relative to ground, as indicated by line 238.

FIG. 2A is a top view of foot 200 showing a typical position of first metatarsal 210 in the transverse plane. The transverse plane, which is also known as the horizontal plane, axial plane, or transaxial plane, is considered any plane that divides the body into superior and inferior parts. On foot 200, the transverse plane is a plane that extends horizontally and is perpendicular to an axis extending dorsally to plantarly (top to bottom) across the foot. FIG. 2A shows first metatarsal 210 with a typical IMA 234 in the transverse plane. FIG. 2B shows first metatarsal 210 with a transverse plane rotational deformity characterized by a greater IMA caused by the distal end of first metatarsal 210 being pivoted medially relative to the second metatarsal 212.

FIG. 3A is a side view of foot 200 showing a typical position of first metatarsal 210 in the sagittal plane. The sagittal plane is a plane parallel to the sagittal suture which divides the body into right and left halves. On foot 200, the sagittal plane is a plane that extends vertically and is perpendicular to an axis extending proximally to distally along the length of the foot. FIG. 3A shows first metatarsal 210 with a typical rotational position in the sagittal plane. FIG. 3B shows first metatarsal 210 with a sagittal plane rotational deformity characterized by a rotational angle 240 relative to ground, as indicated by line 238.

A system and technique that utilizes a compressor-distractor and/or a pin lock according to the disclosure can be useful during a bone positioning procedure, for example, to correct an anatomical misalignment of a bones or bones. In some applications, the compressor-distractor can help establish and/or maintain a realignment between a metatarsal and an adjacent cuneiform. Additionally or alternatively, the compressor-distractor can facilitate clean-up and compression between adjacent bone portions between fixation. The pin lock can help hold the compressor-distractor at an appropriate position along the length of a pin or pins connecting the compressor-distractor to bone portions to be compressed and/or distracted.

The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its *crista* prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

A multi-diameter fixation pin and technique that utilizes a multi-diameter fixation pin according to the disclosure can be useful during a bone positioning procedure, for example, to correct an anatomical misalignment of a bones or bones. In some applications, the multi-diameter fixation pin can be used to help hold a moved position of a metatarsal relative to an adjacent cuneiform. For example, after a metatarsal is moved relative to an adjacent cuneiform, the multi-diameter fixation pin may be inserted into the move metatarsal and adjacent bone (e.g., through a first metatarsal and into an adjacent second metatarsal). This can provide temporary fixation helping to hold the move position of the metatarsal (e.g., first metatarsal) for further procedural steps, such as applying one or more permanent fixation devices (e.g., plate, screw, intramedullary pin).

The metatarsal undergoing realignment may be anatomically misaligned in the frontal plane, transverse plane, and/or sagittal plane, as illustrated and discussed with respect to FIGS. 1-3 above. Accordingly, realignment may involve releasing the misaligned metatarsal for realignment and thereafter realigning the metatarsal in one or more planes, two or more planes, or all three planes. After suitably realigning the metatarsal, the metatarsal can be fixated to hold and maintain the realigned positioned.

While a metatarsal can have a variety of anatomically aligned and misaligned positions, in some examples, the term "anatomically aligned position" means that an angle of a long axis of first metatarsal 210 relative to the long axis of second metatarsal 212 is about 10 degrees or less (e.g., 9 degrees or less) in the transverse plane and/or sagittal plane. In certain embodiments, anatomical misalignment can be corrected in both the transverse plane and the frontal plane. In the transverse plane, a normal IMA 234 between first metatarsal 210 and second metatarsal 212 is less than about 9 degrees. An IMA 234 of between about 9 degrees and about 13 degrees is considered a mild misalignment of the first metatarsal and the second metatarsal. An IMA 234 of greater than about 16 degrees is considered a severe misalignment of the first metatarsal and the second metatarsal. In some embodiments, methods and/or devices according to the disclosure are utilized to anatomically align first metatarsal 210 by reducing the IMA from over 10 degrees to about 10 degrees or less (e.g., to an IMA of 9 degrees or less, or an IMA of about 1-5 degrees), including to negative angles of about −5 degrees or until interference with the second metatarsal, by positioning the first metatarsal at a different angle with respect to the second metatarsal.

With respect to the frontal plane, a normal first metatarsal will be positioned such that its crista prominence is generally perpendicular to the ground and/or its sesamoid bones are generally parallel to the ground and positioned under the metatarsal. This position can be defined as a metatarsal rotation of 0 degrees. In a misaligned first metatarsal, the metatarsal may be axially rotated between about 4 degrees to about 30 degrees or more. In some embodiments, methods and/or devices according to the disclosure are utilized to anatomically align the metatarsal by reducing the metatarsal rotation from about 4 degrees or more to less than 4 degrees (e.g., to about 0 to 2 degrees) by rotating the metatarsal with respect to the adjacent cuneiform.

An example technique utilizing a multi-diameter fixation pin will be described in greater detail below with respect to FIGS. 9-15. However, example multi-diameter fixation pin that may be used according to the disclosure will first be described with respect to FIGS. 4 and 5.

Figure 4:
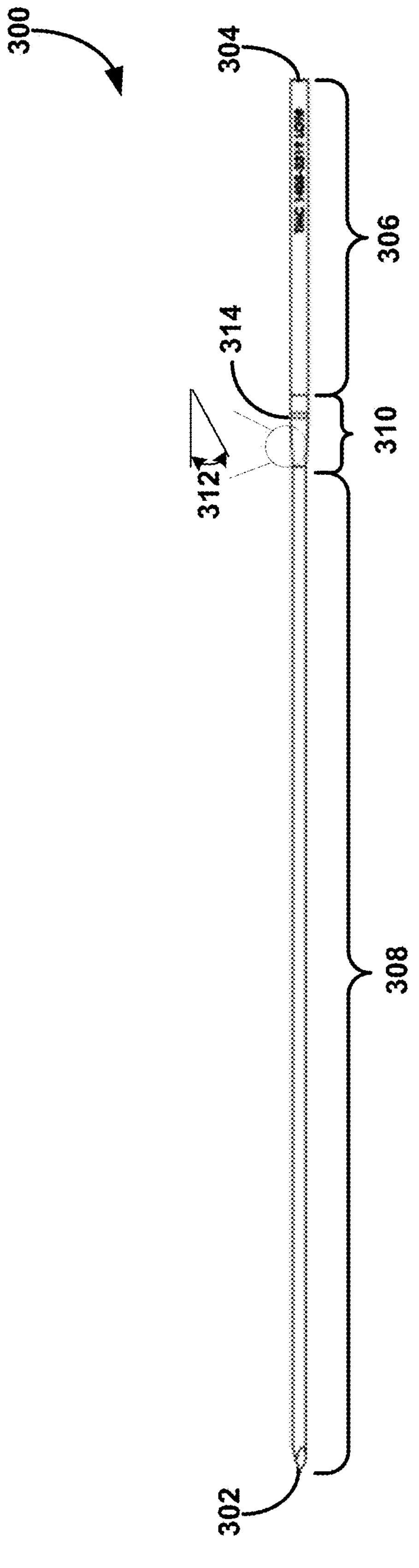
FIG. 4 is an illustration of an example multi-diameter fixation pin according to disclosure.

FIG. 4 is an illustration of an example multi-diameter fixation pin 300 for an orthopedic procedure. Fixation pin 300 has a body extending lengthwise from a first end 302 to a second and 304 at an opposite end of the body. Fixation pin 300 defines a driver engagement portion 306 and a bone insertion portion 308. Driver engagement portion 306 and bone insertion portion 308 may be different portions of the fixation pin having different cross-sectional areas (e.g., diameters).

For example, driver engagement portion 306 of fixation pin 300 can be configured (e.g., sized and/or shaped) for insertion into a powered driver. The driver engagement portion 306 may have a length and diameter that allows the driver engagement portion to be inserted into a powered driver to a depth appropriate for the powered driver to then act on the fixation pin for driving the pin a surgical procedure Bone insertion portion 308 a fixation pin 300 can be configured to be partially or fully inserted into one or more bone portions. For example, bone insertion portion 308 may have a diameter different than driver engagement portion 306. In some implementations, bone insertion portion 308 has a diameter smaller than the diameter of driver engagement portion 306. When so configured, a comparatively larger region a fixation pin 300 defined by driver engagement portion 306 can be inserted into the powered driver. A comparatively smaller region a fixation pin 300 defined by bone insertion portion 308 can be partially or fully inserted into and/or through one or more bone portions.

Depending on the procedure being undertaken, it may be clinically beneficial to insert a comparatively smaller diameter fixation pin into the one or more bone portions than a comparatively larger diameter fixation pin. The smaller diameter fixation pin may cause less bone trauma. Additionally or alternatively, in instances where the fixation pin is inserted into comparatively small bones, such as bones of the foot (e.g., cuneiform, first metatarsal, second metatarsal), a comparatively smaller fixation pin may reduce the tendency of the bone(s) to fracture or break upon insertion of a fixation pin. Such fracturing or breaking may occur when a comparatively large fixation pin is inserted into the bone (s).

While fixation pin 300 is described as having a driver engagement portion 306, it should be appreciated that the entire portion need not be inserted into a driver during a surgical procedure. Rather, driver engagement portion 306 may define a section along the length of fixation pin 300 having a first diameter different than one or more other sections of the fixation pin having one or more other diameters. Driver engagement portion 306 may or may not include second end 304.

Likewise, it should be appreciated that while fixation pin 300 is described as having a bone insertion portion 308, the entire portion need not be inserted into a bone during a surgical procedure. Rather, bone insertion portion 308 may define a section along the length of fixation pin 300 having a second diameter different than driver engagement portion 306. At least part of the length of bone insertion portion 308 may be inserted into and/or through one or more bone portions during a surgical procedure.

Fixation pin 300 in some examples, driver engagement portion 306 and bone insertion portion 308 a fixation pin 300 are immediately adjacent to each other along the length of the fixation pin. A sharp (e.g., 90 degree) transition may be provided between driver engagement portion 306 and bone insertion portion 308, such as a dimensional instep or out step between the two differently sized portions. In other configurations, fixation pin 300 to define a taper portion between driver engagement portion 306 and bone insertion portion 308. The taper portion may be a region of dimensional transition between the cross-sectional size of driver engagement portion 306 and the cross-sectional size of bone insertion portion 308.

In the example of FIG. 4, fixation pin 300 is illustrated as including a taper portion 310 sandwiched between driver engagement portion 306 and bone insertion portion 308. Taper portion 310 can have a size (e.g., diameter) that transitions from the cross-sectional size of driver engagement portion 306 to the cross-sectional size of bone insertion portion 308. Taper portion 310 may taper at any suitable angle 312. In some implementations, angle 312 ranges from 5° to 75°, such as from 10° to 60°, or from 15° to 45°.

In some examples, fixation pin 300 may include an indicator 314 positioned at a location along the length of the fixation pin. Indicator 314 may designate how deep fixation pin 300 can be inserted into a powered driver. For example, in use, a clinician may insert second end 304 of fixation pin 300 into a powered driver and advance the fixation pin deeper into the body (e.g., collet) up to indicator. The clinician may not advance fixation pin 300 beyond indicator 314 into the driver. When configured with indicator 314, the indicator may be implemented in a variety of different ways. As one example, a color band or marking may be provided on a perimeter surface of fixation pin 300. As another example, a notch may be formed in a perimeter surface of fixation pin 300. For instance, a laser scribe may be formed partially or fully about a circumferential perimeter of fixation pin 300 to define indicator 314.

As noted, multi-diameter fixation pin 300 includes first end 302. First end 302 is the leading end of the fixation pin that is inserted into bone during a procedure. In some examples, first end 302 is tapered/sharpened to a point or rounded. This may help case insertion of the pin during a surgical procedure. In other examples, first end 302 of fixation pin 300 is not shaped relative to a remainder of bone insertion portion 308.

The specific dimensions of fixation pin 300 can vary depending on the needs of the clinician in the desired procedure in which the fixation pin is going to be utilized. In some examples, driver engagement portion 306 of fixation pin 300 is sized to have a same diameter as one or more other pins used in a surgical procedure (wherein the pins have a constant diameter across their length instead of having multiple diameters). Additionally or alternatively, driver engagement portion 306 of fixation pin 300 may be sized to have a diameter that is different than but sufficiently close to the diameter of one or more other pins used in the surgical procedure such that the fixation pin can be inserted into bone using the same powered driver hardware used to insert the one or more other pins.

Bone insertion portion 308 can have a different diameter (e.g., smaller diameter) than driver engagement portion 306. The diameter of bone insertion portion 308 may be sufficiently different than the diameter of driver engagement portion 306 such that, if the entire length of fixation pin 300 had the diameter of bone insertion portion 308, the fixation pin could not be inserted into bone using the same powered driver hardware used to insert the one or more other pins used in a surgical procedure (wherein the pins have a constant diameter across their length instead of having multiple diameters).

As examples, driver engagement portion 306 may define a first diameter greater than or equal to 2.0 mm, such as a diameter within a range from 2.0 mm to 3.2 mm. Bone insertion portion 308 may define a second diameter less than 2.0 mm, such as a diameter within a range from 0.7 mm to 1.8 mm. Independent of the specific diameters of driver engagement portion 306 and bone insertion portion 308, the difference between the diameters of the two portions may be at least 0.1 mm, such as at least 0.2 mm, or at least 0.5 mm. For example, the difference between the diameters of driver engagement portion 306 and bone insertion portion 308 may range from 0.1 mm to 1.5 mm, such as from 0.2 mm to 0.5 mm.

One or more other pins used in a surgical procedure with fixation pin 300 (wherein the one or more other pins have a constant diameter across their length instead of having multiple diameters) can have a diameter the same as and/or within the same range of as those listed above with respect to driver engagement portion 306. In some examples, the one or more other pins used in the surgical procedure have a diameter that differs from the diameter of driver engagement portion 306 by less than 0.5 mm, such as less than 0.2 mm.

The overall length of multi-diameter fixation pin 300 from first end 302 to second end 304 can also vary depending on the desired clinical application. In different examples, fixation pin 300 may have a length within a range from 25 mm to 500 mm, such as from 50 mm to 260 mm. Further, while fixation pin 300 may typically have a circular cross-sectional shape, the fixation pin can have any polygonal (e.g., square, rectangle) or arcuate (e.g., curved, elliptical) shape.

Fixation pin 300 may be formed as a unitary body from a single piece of material, e.g., via casting, molding, and/or milling. Alternatively, fixation pin 300 may be formed from multiple segments of material (e.g., materials having different diameters) that are then joined together to form a unitary body (e.g., via welding or other permanent joining) technique. In general, fixation pin 300 can be formed from a biocompatible material. Example materials that may be used to fabricate fixation pin 300 include steel (e.g., stainless steel), titanium, ceramic materials, biocompatible plastics, and combinations thereof. After fabrication, fixation pin 300 may be packaged and sterilized, e.g., chemically and/or thermally. Fixation pin 300 may be packaged alone or as part of a kit that includes one or more other pins and/or other instruments used during a surgical procedure.

Multi-diameter fixation pin 300 can be inserted into one or more bone portions using a powered driver. The powered driver may receive the fixation pin by inserting driver engagement portion 306 into the driver and then applying a force to the pin to drive bone insertion portion 308 of the pin into and/or through one or more bone portions. The powered driver may apply a rotary force, causing rotation of the fixation pin, and/or an axial impact force to drive the pin actually into the bone.

Figure 5:
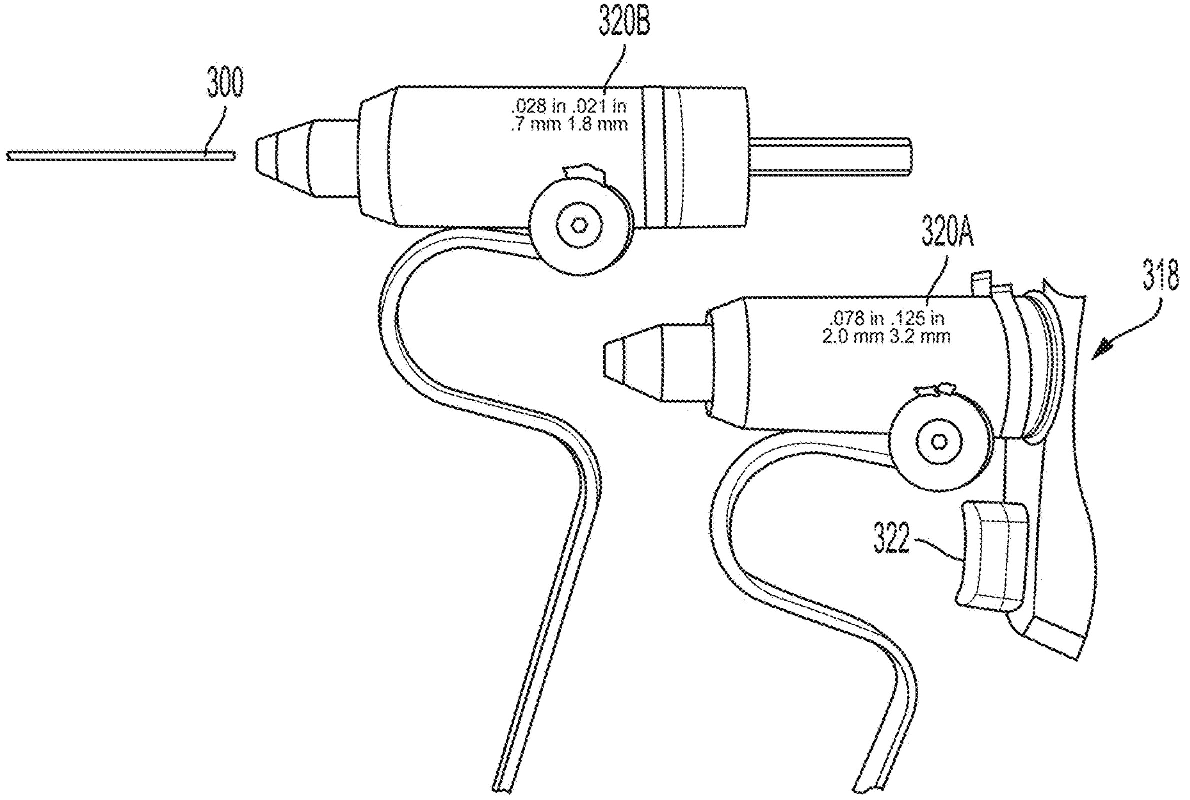
FIG. 5 is an illustration of an example powered driver system that can be used to drive the multi-diameter fixation pin of FIG. 4.

FIG. 5 is an illustration of an example system that includes a powered driver 318 that can be used to insert fixation pin 300. Powered driver 318 in this example is shown with interchangeable collets 320A and 320B (collectively referred to as "collet 320"). Collet 320 may be a chuck that forms a collar around an object (e.g., fixation pin 300 and one or more other fixation pins optionally used during a surgical procedure) and can exert a clamping force on the object. Collet 320 can have a sleeve with a cylindrical inner surface. The collet may be squeezed against a matching taper such that its inner surface contracts to a slightly smaller diameter, squeezing a pin inserted therein to hold the pin securely.

Powered driver 318 can have an integral collet 320 that can only receive a specific size or range of sizes of fixation pins. Alternatively, powered driver 318 can have interchangeable collets 320, each of which is configured to receive a different specific size or range of sizes of fixation pins.

Powered driver 318 can be powered by any motive energy, such as a pneumatic energy or electrical energy. To engage powered driver 318, the clinician may depress trigger 322 to drive a fixation pin 300 inserted into the powered driver into a bone. While fixation pin 300 is generally described as being inserted into a bone using a powered driver, such as powered driver 318, it should be appreciated that a fixation pin according to disclosure is not limited to such an example insertion device. For example, the multi-diameter fixation pin can be inserted using hand force or a powered driver having a different configuration than that illustrated and described with respect to FIG. 5.

In some examples, a multi-diameter fixation pin is used as part of a metatarsal realignment procedure in which a metatarsal is realigned relative to an adjacent cuneiform and/or metatarsal in one or more planes, such as two or three planes. Additional details on example bone realignment techniques and devices with which the multi-diameter fixation pin may be used are described in U.S. Pat. No. 9,622,805, titled "BONE POSITIONING AND PREPARING GUIDE SYSTEMS AND METHODS," filed on Dec. 28, 2015 and issued Apr. 18, 2017, and U.S. Pat. No. 9,936,994, titled "BONE POSITIONING GUIDE," filed on Jul. 14, 2016 and issued on Apr. 10, 2018, and US Patent Publication No. 2017/0042599 titled "TARSAL-METATARSAL JOINT PROCEDURE UTILIZING FULCRUM," filed on Aug. 14, 2016. The entire contents of each of these documents are hereby incorporated by reference.

A multi-diameter fixation pin can be used in any desired orthopedic procedure, and the disclosure is not limited to any particular procedure. In some implementations, however, the multi-diameter fixation pin is used as part of a metatarsal realignment procedure. The metatarsal realignment procedure may or may not utilize one or more other surgical instruments, such as a bone positioning guide and/or a bone preparation guide.

Figure 6:
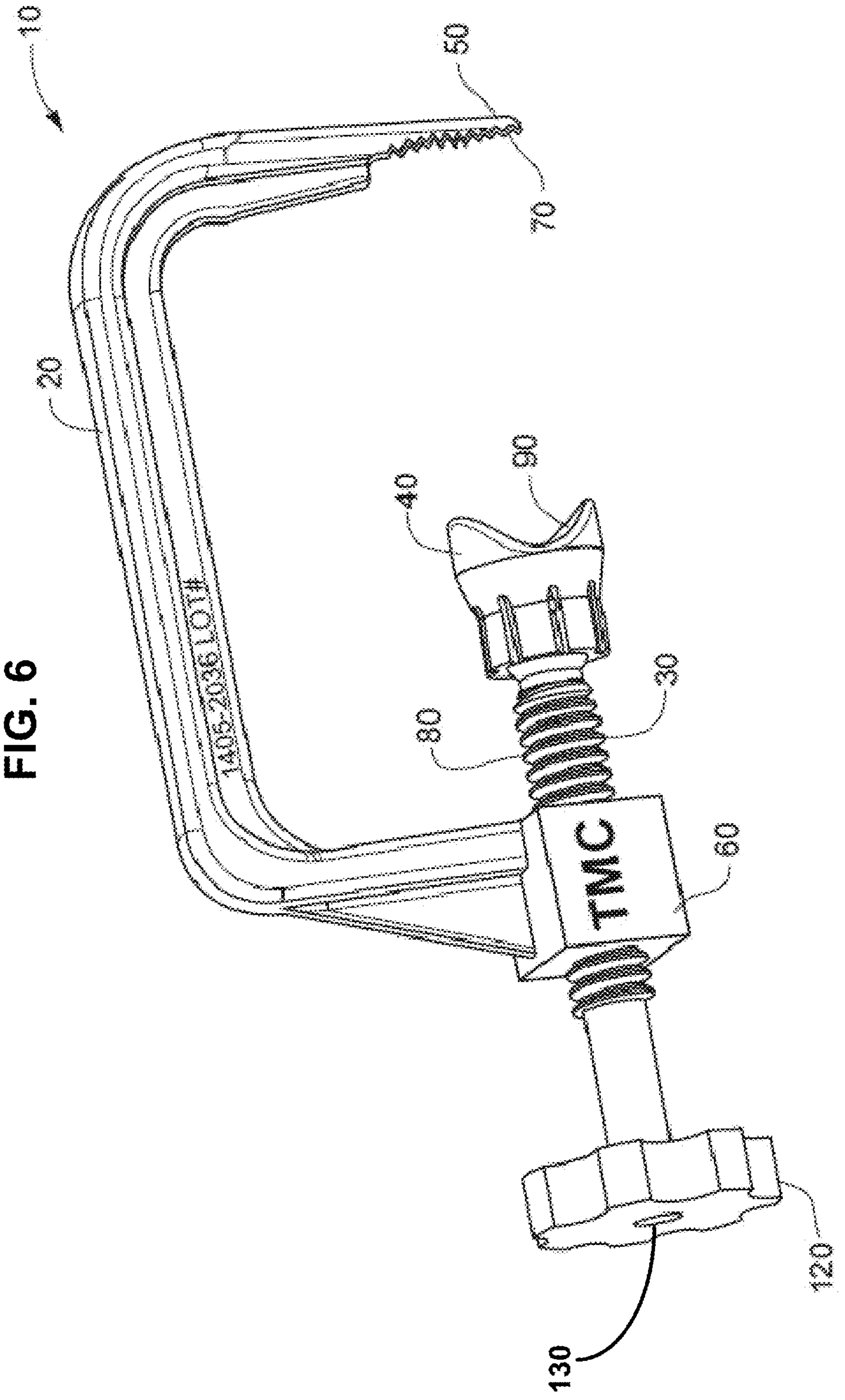
FIG. 6 is a side perspective view of an example bone positioning guide that can be used with a multi-diameter fixation pin.

FIG. 6 illustrates an example bone positioning guide 10 that may be used as part of a surgical procedure involving a multi-diameter fixation pin 300. In this example a bone positioning guide 10 includes a main body member 20 and a shaft 30. The bone engagement member 40 is connected to the shaft and a tip 50 is connected to the main body member. In general, the main body member 20 can be sized and shaped to clear anatomy or other instrumentation (e.g., pins and guides) while positioned on a patient. Main body member 20 is illustrated as having a generally C-shaped configuration with a first end 60 and a second end 70.

Shaft 30 can be movably connected to the main body member 20 proximate its first end 60. In some embodiments, the shaft 30 includes threads 80 that engage with the main body member 20 such that rotation of the shaft translates the shaft with respect to the main body member. In other embodiments, the shaft can slide within the main body member and can be secured thereto at a desired location with a set screw. In yet other embodiments, the shaft can be moved with respect to the main body by a ratchet mechanism. In the embodiment shown, the shaft moves along an axis that intersects the tip 50.

Bone positioning guide 10 can include a bone engagement member 40 having a surface 90 configured to contact a bone, such as a metatarsal or a cuneiform. In the embodiment shown, the surface 90 is concave. Such a surface is adapted to promote surface contact with a generally cylindrical bone, such as a metatarsal. In use, bone engagement member 40 can be positioned in contact with a first bone portion (e.g., a first metatarsal) and tip can be positioned in contact with a second bone portion, such as an adjacent bone (e.g., second metatarsal or third metatarsal). Bone positioning guide 10 can include an actuator (e.g., a knob or a handle) 120 to actuate the positioning guide and move bone engagement member 40 relative to tip 50. In the embodiment shown, the actuator can be useful for allowing a user to rotate the shaft with respect to the main body member 20.

In some configurations, bone positioning guide 10 includes a cannulation 130, such as a cannulation 130 extending through the actuator, shaft, and bone engagement member. Multi-diameter fixation pin 300 can be placed through cannulation 130 and into contact with or through a bone engaged with the bone engagement member. For example, fixation wire 300 can be placed into the bone engaged with bone engagement member 40 to fix the position of the bone engagement member with respect to the bone. In another example, fixation wire 300 can be placed through the bone in contact with the bone engagement member and into an adjacent bone (e.g., second metatarsal) to maintain a bone position of the bone in contact with the bone engagement member and the adjacent bone. Fixation pin 300 can be inserted through cannulation 130 and into one or more bone portions using powered driver 318.

Figure 7:
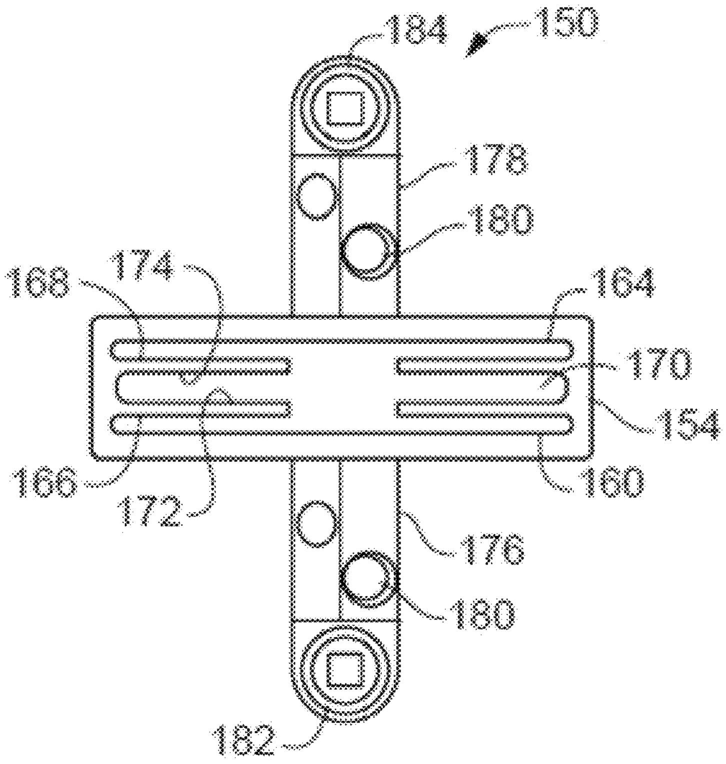
FIG. 7 is a top plan view of an example bone preparation guide that can be used with a multi-diameter fixation pin.

FIG. 7 illustrates an example bone preparation guide 150 that may be used as part of a surgical procedure involving a multi-diameter fixation pin 300. In some examples, bone preparation guide 150 includes a body 154 defining a first guide surface 160 to define a first preparing plane and a second guide surface 164 to define a second preparing plane. A tissue removing instrument (e.g., a saw, rotary bur, osteotome, etc., not shown) can be aligned with the surfaces to remove tissue (e.g., remove cartilage or bone and/or make cuts to bone). The first and second guide surfaces 160, 164 can be spaced from each other by a distance, (e.g., between about 2 millimeters and about 10 millimeters, such as between about 4 and about 7 millimeters). In the embodiment shown, the first and second guide surfaces are parallel, such that cuts to adjacent bones using the guide surfaces will be generally parallel.

In some configurations, as shown in FIG. 7, a first facing surface 166 is positioned adjacent the first guide surface 160 and/or a second facing surface 168 is positioned adjacent the second guide surface 164. In such configurations, the distance between the first guide surface and the first facing surface defines a first guide slot, and the distance between the second guide surface and the second facing surface defines a second guide slot. Each slot can be sized to receive a tissue removing instrument to prepare the bone ends. The first and second slots may be parallel or skewed. In the illustrated example, the facing surfaces each contain a gap, such that the surface is not a single, continuous surface. In other embodiments, the facing surfaces can be a single, continuous surface lacking any such gap.

An opening 170 can be defined by the body 154 between the first and second guide surfaces. The opening can be an area between the guide surfaces useful for allowing a practitioner to have a visual path to bones during bone preparation and/or to receive instruments. In the configuration shown, the opening extends across the body and a distance from a surface 172 opposite of the first facing surface 166 to a surface 174 opposite of the second facing surface 168.

The illustrated bone preparation guide also includes a first end 176 extending from the body 154 in a first direction and a second end 178 extending from the body in a second direction. The second direction can be different than the first direction (e.g., an opposite direction). As shown, each of the first end and the second end can include at least one fixation aperture 180 configured to receive a fixation pin to secure the bone preparation guide to an underlying bone. For example, first end 176 of bone preparation guide 150 may define a first fixation aperture through which a first pin is inserted and the second end 178 of bone preparation guide 150 may define a second fixation aperture through which a second pin is inserted. The first and second pins may be inserted using powered driver 318 and may have a constant diameter across their length. The first end 176 and/or the second end 178 of bone preparation guide 150 may also defined one or more additional fixation apertures that are angled (at a non-zero degree angle) or otherwise skewed relative to the two parallel fixation apertures.

In use, a clinician may insert the two pins (e.g., parallel pins) through fixation apertures 180 and may optionally insert one or more angled pins through the one or more angled fixation apertures. This combination of parallel and angled pins may prevent bone preparation guide 150 from being removed from the underlying bones being worked upon.

Figure 13:
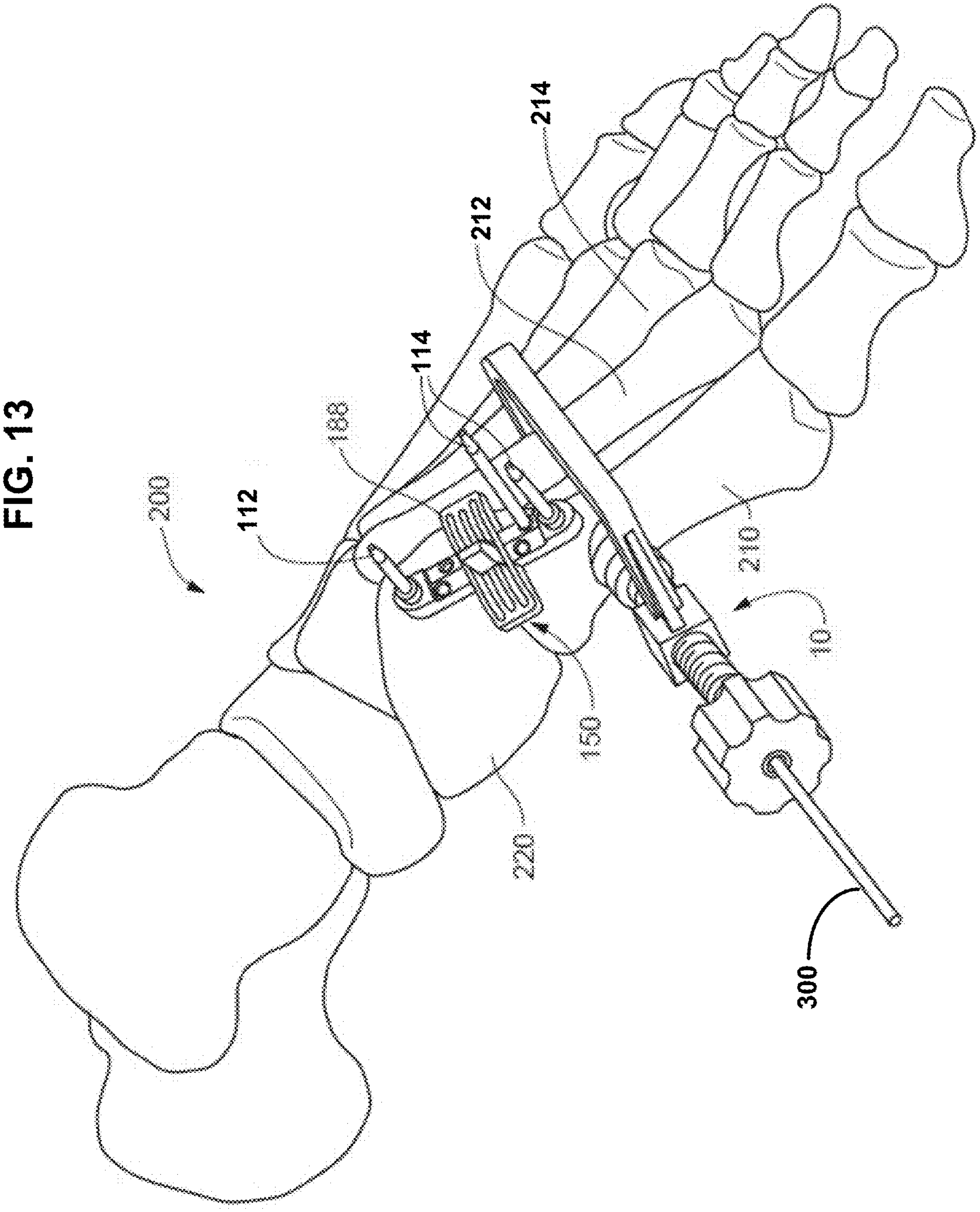
FIG. 13 is a perspective view of a foot depicting a bone preparation guide on the foot with pins inserted through the bone preparation guide.

In some examples as shown in FIG. 13, bone preparation guide 150 can also include a first adjustable stabilization member 182 engaged with the first end 176 and/or a second adjustable stabilization member 184 engaged with the second end 178. Each of the members can be threaded and engage a threaded aperture defined by the ends. The elevation of each end can be adjusted with respect to a bone by adjusting the stabilization member. In some embodiments, as shown, the stabilization members are cannulated such that they can receive a fixation pin.

Figure 8:
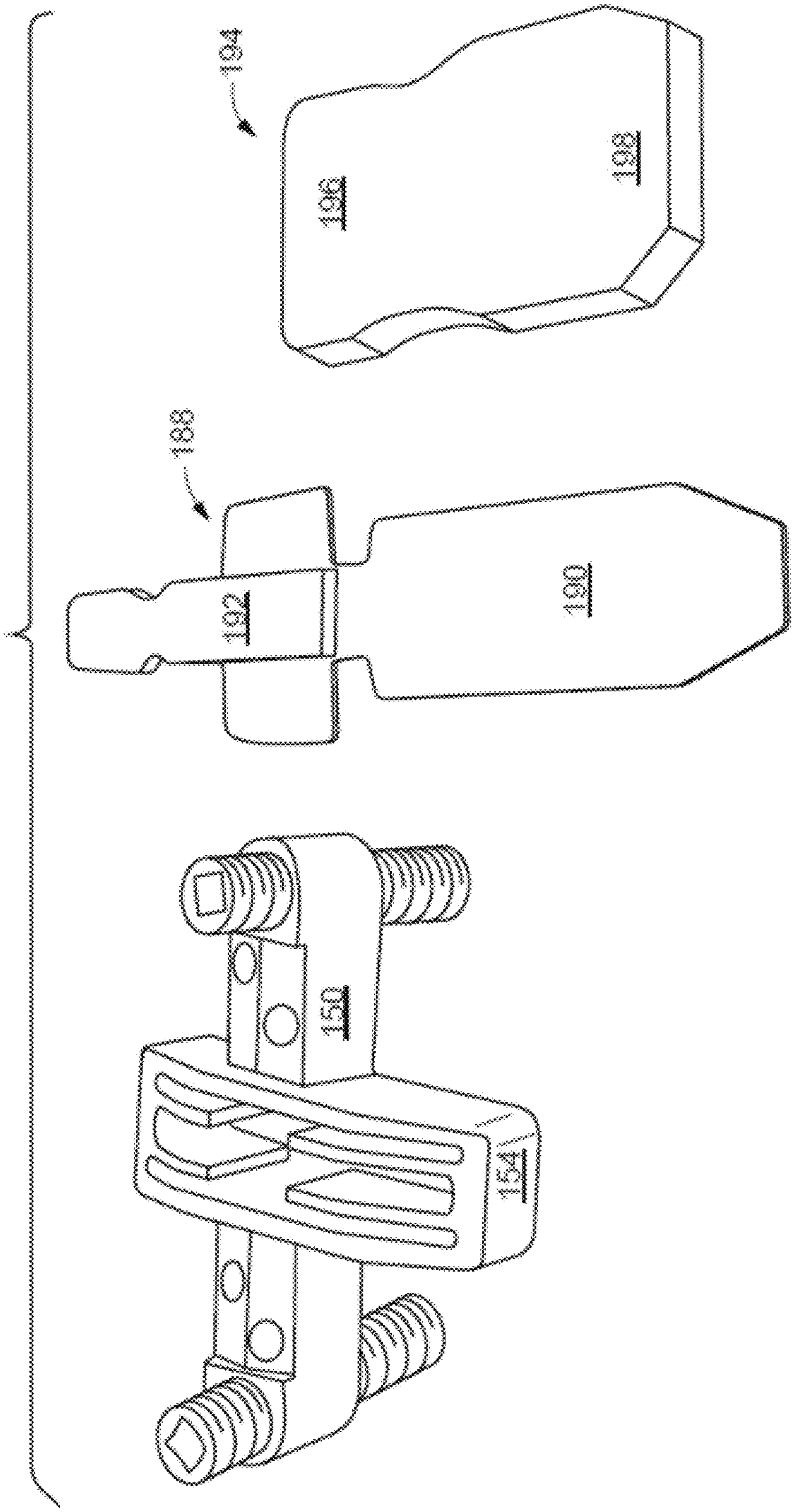
FIG. 8 is a perspective view of an example bone preparing guide, spacer, and tissue removing instrument check member that can be used with a multi-diameter fixation pin.

With reference to FIG. 8, bone preparation guide 150 may include or be used with a spacer 188 that extends downward from the body 154. Spacer 188 may be configured to be placed into a joint (e.g., within the TMT joint). In some embodiments, the spacer 188 is selectively engageable with the body of the bone preparation guide and removable therefrom. The spacer can have a first portion 190 configured to extend into a joint space and a second portion 192 engageable with the body 154. In the embodiment shown, the spacer can be received within opening 170, such that the spacer extends from the body in between the first and second guide surfaces. Such a spacer can be useful for positioning the body at a desired position with respect to a joint and for properly positioning the guide with respect to bones to be cut in more than one plane (e.g., three planes selected from more than one of a frontal plane, a transverse plane, and a sagittal plane). The distance between the spacer and the first guide surface can define a length of tissue removal (e.g., bone or cartilage to be cut) from a first bone, and the distance between the spacer and the second guide surface can define a length of tissue removal (e.g., bone or cartilage to be cut) from a second bone.

As also shown in FIG. 8, bone preparation guide 150 may include or be used with a tissue removal location check member 194. Tissue removal check member 194 may be engageable with the body 154 and configured to extend to a first bone and a second bone. The tissue removal location check member can have a first portion 196 configured to extend into contact with first and second bones and a second portion 198 engageable with the body. In the embodiment shown, the tissue removal check member 194 is configured to extend in the body 154 at both the first and second guiding surfaces. The tissue removal location check member 194 may be useful for allowing a practitioner to see where a tissue removing instrument guided by the surfaces will contact the bone to be prepared.

Bone preparation facilitated by bone preparation guide 150 can be useful, for instance, to facilitate contact between leading edges of adjacent bones, separated by a joint, or different portions of a single bone, separated by a fracture, such as in a bone alignment and/or fusion procedure. A bone may be prepared using one or more bone preparation techniques. In some applications, a bone is prepared by cutting the bone. The bone may be cut transversely to establish a new bone end facing an opposing bone portion. Additionally or alternatively, the bone may be prepared by morselizing an end of the bone. The bone end can be morselized using any suitable tool, such as a rotary bur, osteotome, or drill. The bone end may be morselized by masticating, fenestrating, crushing, pulping, and/or breaking the bone end into smaller bits to facilitate deformable contact with an opposing bone portion.

During a surgical technique utilizing fixation pin 300, a bone may be moved from an anatomically misaligned position to an anatomically aligned position with respect to another bone. Further, both the end of the moved bone and the facing end of an adjacent end may be prepared for fixation. In some applications, the end of at least one of the moved bone and/or the other bone is prepared after moving the bone into the aligned position. In other applications, the end of at least one of the moved bone and/or the other bone is prepared before moving the bone into the aligned position.

Movement of one bone relative to another bone can be accomplished using one or more instruments and/or techniques. In some examples, bone movement is accomplished using a bone positioning device that applies a force to one bone at a single location, such that the bone both translates and rotates in response to the force. This may be accomplished, for example, using a bone positioning guide that includes a bone engagement member, a tip, a mechanism to urge the bone engagement member and the tip towards each other, and an actuator to actuate the mechanism. Additionally or alternatively, bone movement may be accomplished using a compressor-distractor. As yet a further addition or alternative, a clinician may facilitate movement by physically grasping a bone, either through direct contact with the bone or indirectly (e.g., by inserting a K-wire such as fixation pin 300, grasping with a tenaculum, or the like), and moving his hand to move the bone.

An example method for preforming a bone alignment procedure utilizing a compressor-distractor and instrument defining a sliding surface according to the disclosure will now be described with respect to FIGS. 9-15 depicting a foot 200 having a first metatarsal 210, a medial cuneiform 222, and a second metatarsal 212. Unless otherwise indicated, the example steps described can be carried out in any order and need not be performed in the order described.

Figure 9:
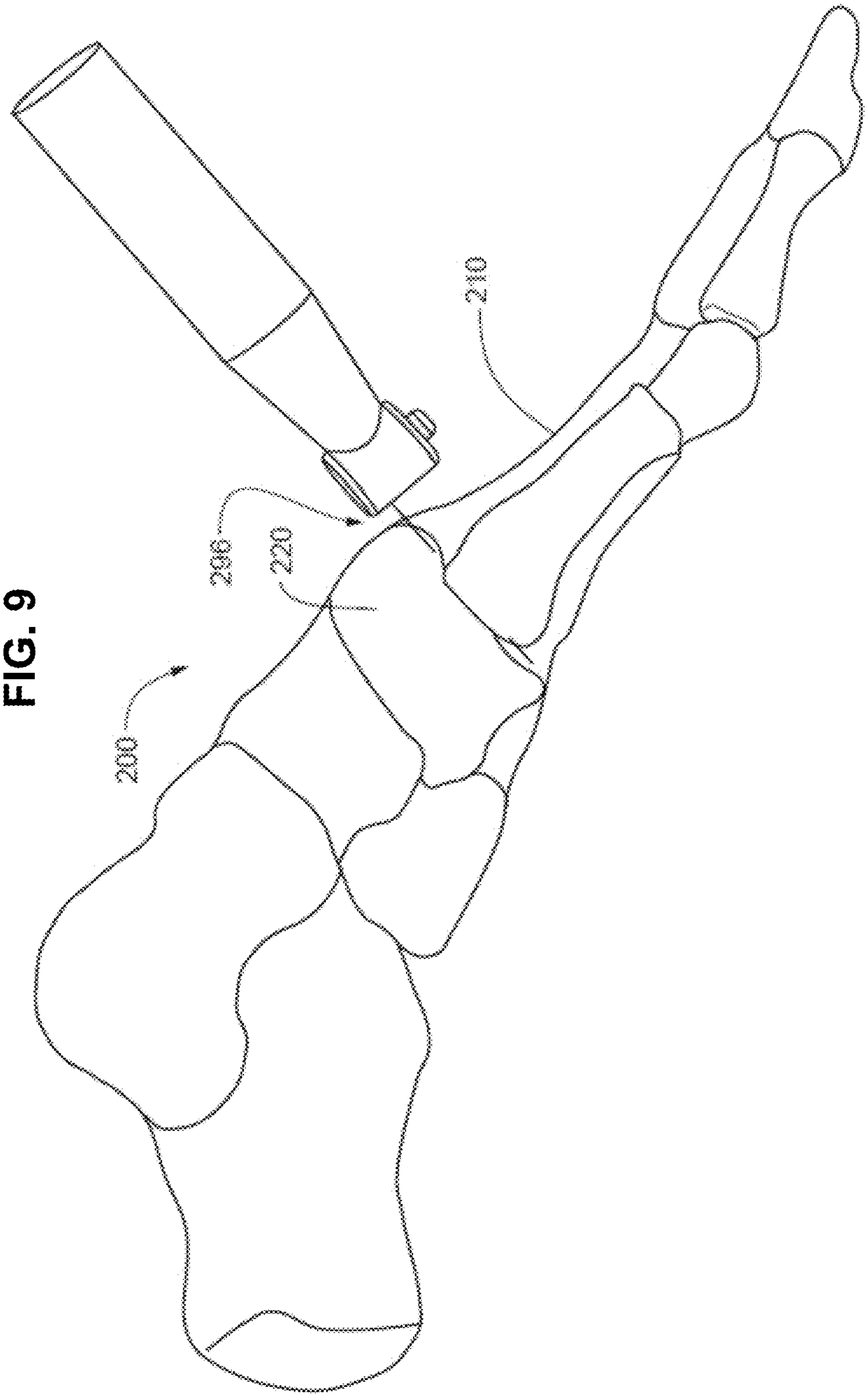
FIG. 9 is a perspective view of a foot depicting a bone positioning guide on the foot prior to an alignment of a first metatarsal.

After customary surgical preparation and access, a bone preparation instrument 296 can be inserted into the joint (e.g., first tarsal-metatarsal joint) to release soft tissues and/or excise the plantar flare from the base of the first metatarsal 210, as shown in FIG. 9. Excising the plantar flare may involve cutting plantar flare off the first metatarsal 210 so the face of the first metatarsal is generally planar. This step helps to mobilize the joint to facilitate a deformity correction. In some embodiments, the dorsal-lateral flare of the first metatarsal may also be excised to create space for the deformity correction (e.g., with respect to rotation of the first metatarsal). In certain embodiments, a portion of the metatarsal base facing the medial cuneiform can be removed during this mobilizing step.

Figure 10:
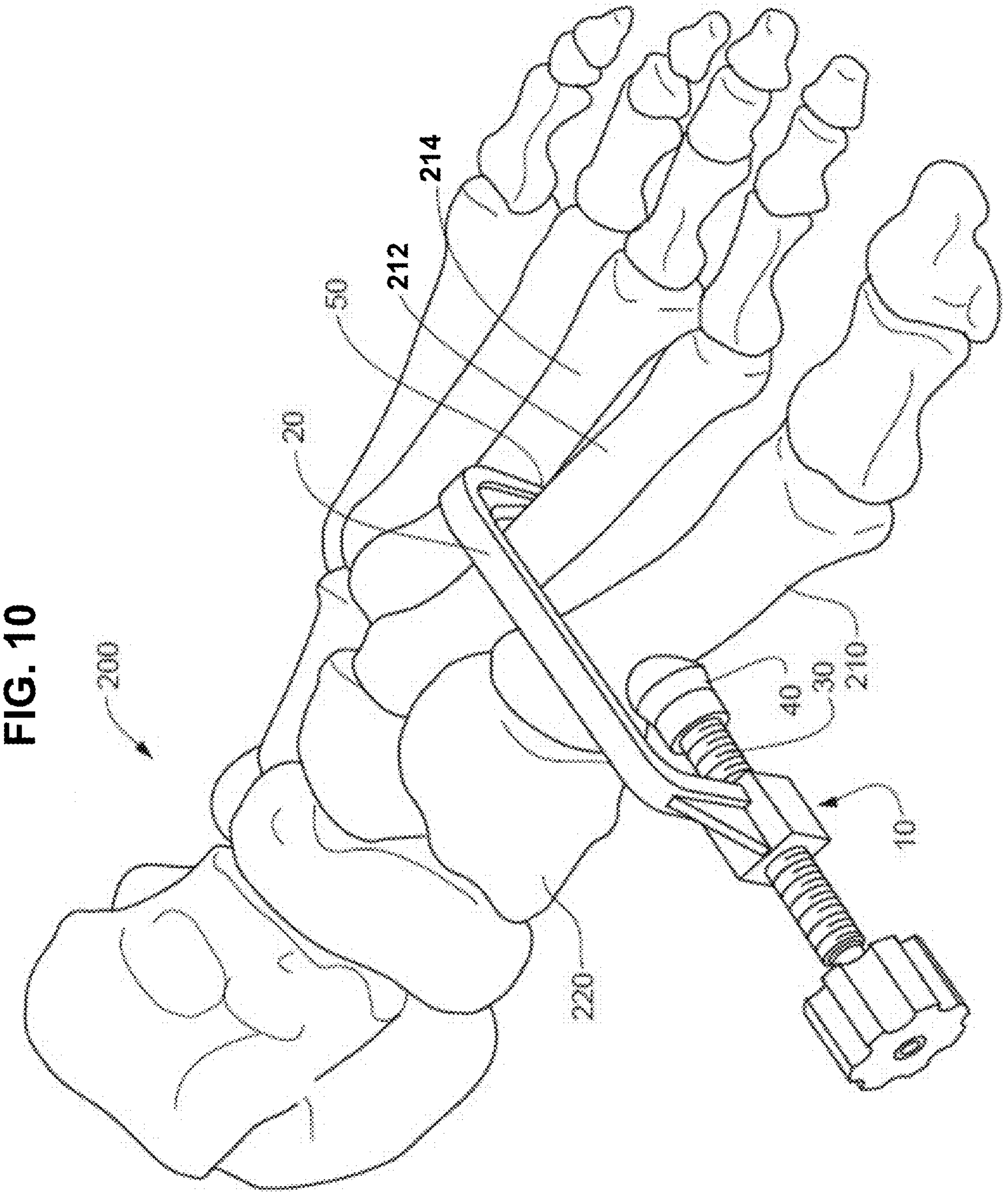
FIG. 10 is a perspective view of a foot depicting a bone positioning guide on the foot.

An incision can be made and, if a bone positioning instrument is going to be used, a tip 50 of a bone positioning guide 10 inserted on the lateral side of a metatarsal other than the first metatarsal 210, such as the second metatarsal 212. As shown in FIG. 10, the tip can be positioned proximally at a base of the second metatarsal 212 and a third metatarsal 294 interface. A surface of a bone engagement member 40 can be placed on the proximal portion of the first metatarsal 210. In some embodiments, the bone engagement member engages a medial ridge of the first metatarsal 210. As shown, the body 20 of the positioning guide can be generally perpendicular to the long axis of the second metatarsal 212.

To help avoid a base shift, a clinician can insert a fulcrum in the notch between first metatarsal 210 and second metatarsal 212 at the base of the metatarsals (e.g., adjacent respective cuneiform) before actuating bone positioning guide 10 or otherwise moving the first metatarsal relative to the medial cuneiform. The fulcrum can provide a point about which first metatarsal 210 can rotate and/or pivot while helping minimize or avoid base compression between the first metatarsal and the second metatarsal.

In applications utilizing bone positioning guide 10, the actuator on the bone positioning guide can be actuated to reduce the angle (transverse plane angle between the first metatarsal and the second metatarsal) and rotate the first metatarsal about its axis (frontal plane axial rotation). The first metatarsal 210 can be properly positioned with respect to the medial cuneiform 222 by moving the bone engagement member 40 bone positioning guide with respect to the tip 50 of the bone positioning guide. In some embodiments, such movement simultaneously pivots the first metatarsal with respect to the cuneiform and rotates the first metatarsal about its longitudinal axis into an anatomically correct position to correct a transverse plane deformity and a frontal plane deformity. Other instrumented and/or non-instrumented approaches can be used to adjustment position of first metatarsal 210 relative to medial cuneiform 222. Thus, other applications utilizing compressor-distractor 100 and a pin lock may be performed without utilizing bone positioning guide 10.

Figure 11:
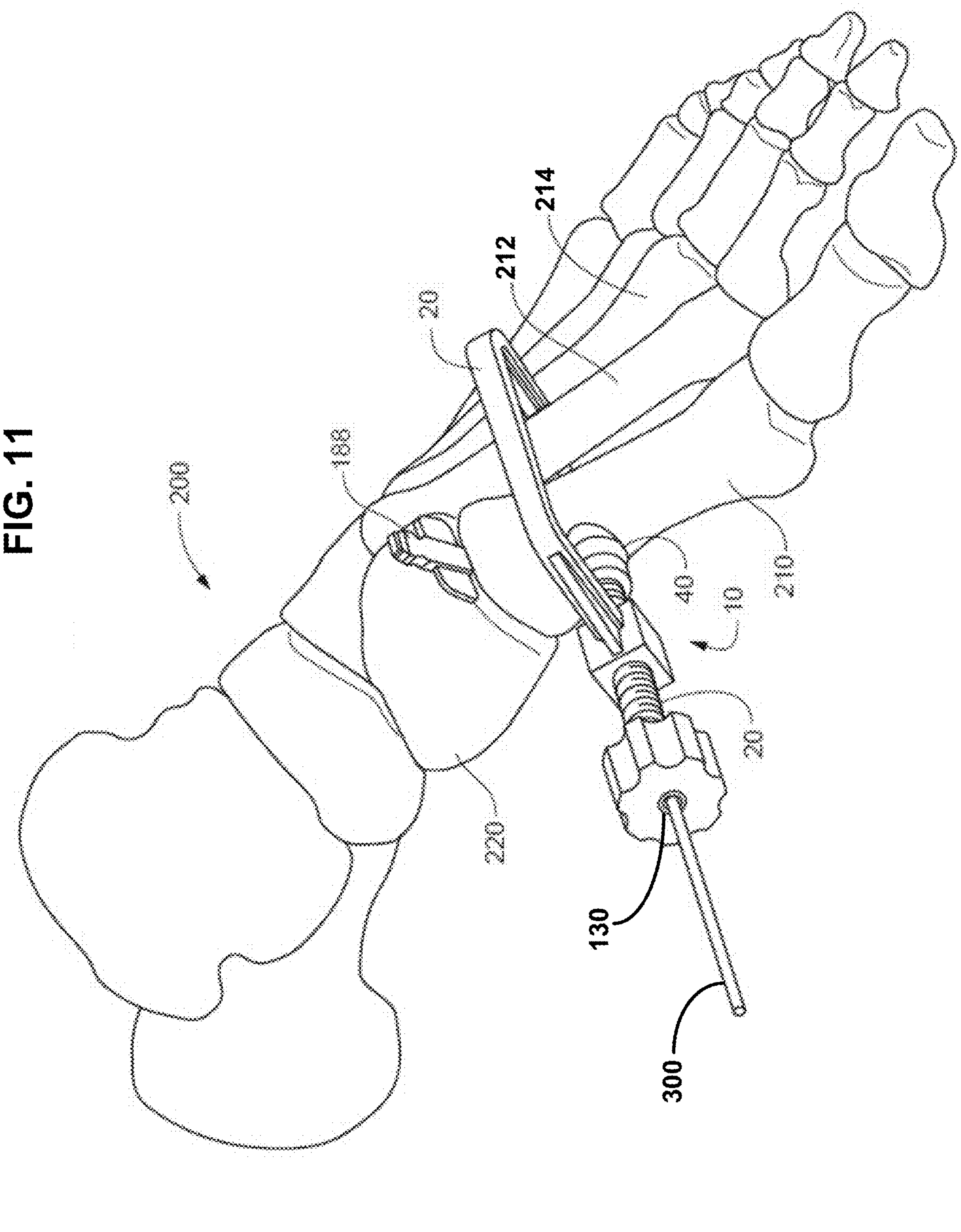
FIG. 11 is a perspective view of a foot depicting a bone positioning guide on the foot after an alignment of a first metatarsal and with a spacer inserted into a joint space.

Independent of whether bone positioning guide 10 is used, an example technique may include inserting fixation pin 300 into and through first metatarsal 210 into an adjacent bone, such as second metatarsal 212 and/or medial cuneiform 220. The clinician may insert driver engagement portion 306 of fixation pin 300 into powered driver 318 and use the driver to drive the bone insertion portion of the pin into first metatarsal 210. The clinician may drive bone insertion portion 308 through cannulation 130, through first metatarsal 210, and into second metatarsal 212, as illustrated in FIG. 11. The clinician may detach powered driver 318, leaving fixation pin 300 in the bones to temporarily fixate the moved position of the first metatarsal.

Figure 12:
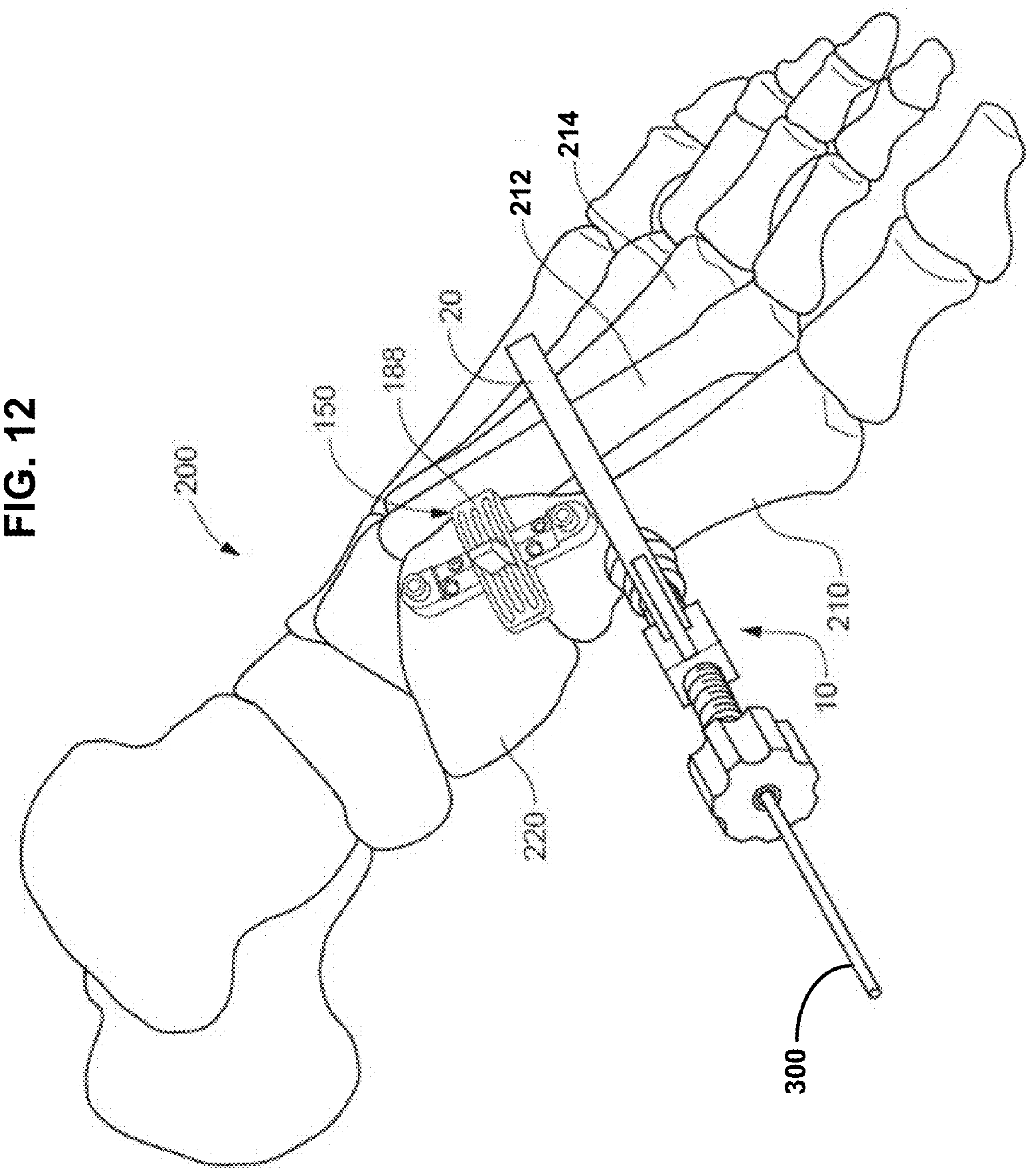
FIG. 12 is a perspective view of a foot depicting a bone preparation guide positioned on the foot.

As also illustrated in FIG. 11, the example technique may involve positioning joint spacer 188 within the joint between first metatarsal 210 and medial cuneiform 222. Bone preparation guide 150 can be placed over the joint spacer 188 as shown in FIG. 12 and engaged with the joint spacer to set a position and orientation of the bone preparation guide relative to the joint. In other embodiments, bone preparation guide 150 is placed on the bones without using joint spacer 188 to aid with positioning.

As depicted in FIG. 13, one or more fixation pins can be inserted into apertures of the bone preparation guide 150 to secure the guide to the first metatarsal 210 and the medial cuneiform 222. The fixation pins inserted into the apertures of bone preparation guide 150 includes a first fixation pin 112 and second fixation pin 114. The first and second fixation pins may or may not be multi-diameter fixation pins. For example, the first and second fixation pins may have a constant diameter across their length. The clinician may insert first and second fixation pins 112, 114 using the same driver 318 and same collet 320 used to insert fixation pin 300. One or more additional pins can be inserted at an angle or in a converging orientation to help prevent movement of the bone preparation guide 150 during a tissue removing step. After insertion of the pins, the spacer 188 (if used) can optionally be removed in embodiments having a selectively engageable spacer.

In some applications, the end of the first metatarsal 210 facing the medial cuneiform 222 can be prepared with a tissue removing instrument 296 guided by a guide surface of bone preparation guide 150 (e.g., inserted through a slot defined by a first guide surface and a first facing surface). In some embodiments, the first metatarsal 210 end preparation is done after at least partially aligning the bones, e.g., by actuating bone positioning guide 10 or otherwise moving the first metatarsal but after preparing the end of first metatarsal 210. In other embodiments, the first metatarsal 210 end preparation is done before the alignment of the bones.

In addition to preparing the end of first metatarsal 210, the end of the medial cuneiform 222 facing the first metatarsal 210 can be prepared with the tissue removing instrument 296 guided by a guide surface of bone preparation guide 150 (e.g., inserted through a slot defined by a second guide surface and a second facing surface). In some embodiments, the medial cuneiform 222 end preparation is done after the alignment of the bones. In yet other embodiments, the medial cuneiform 222 end preparation is done before the alignment of the bones. In embodiments that include cutting bone or cartilage, the cuneiform cut and the metatarsal cut can be parallel, conforming cuts. In some examples, a saw blade can be inserted through a first slot to cut a portion of the medial cuneiform and the saw blade can be inserted through a second slot to cut a portion of the first metatarsal.

Figure 14:
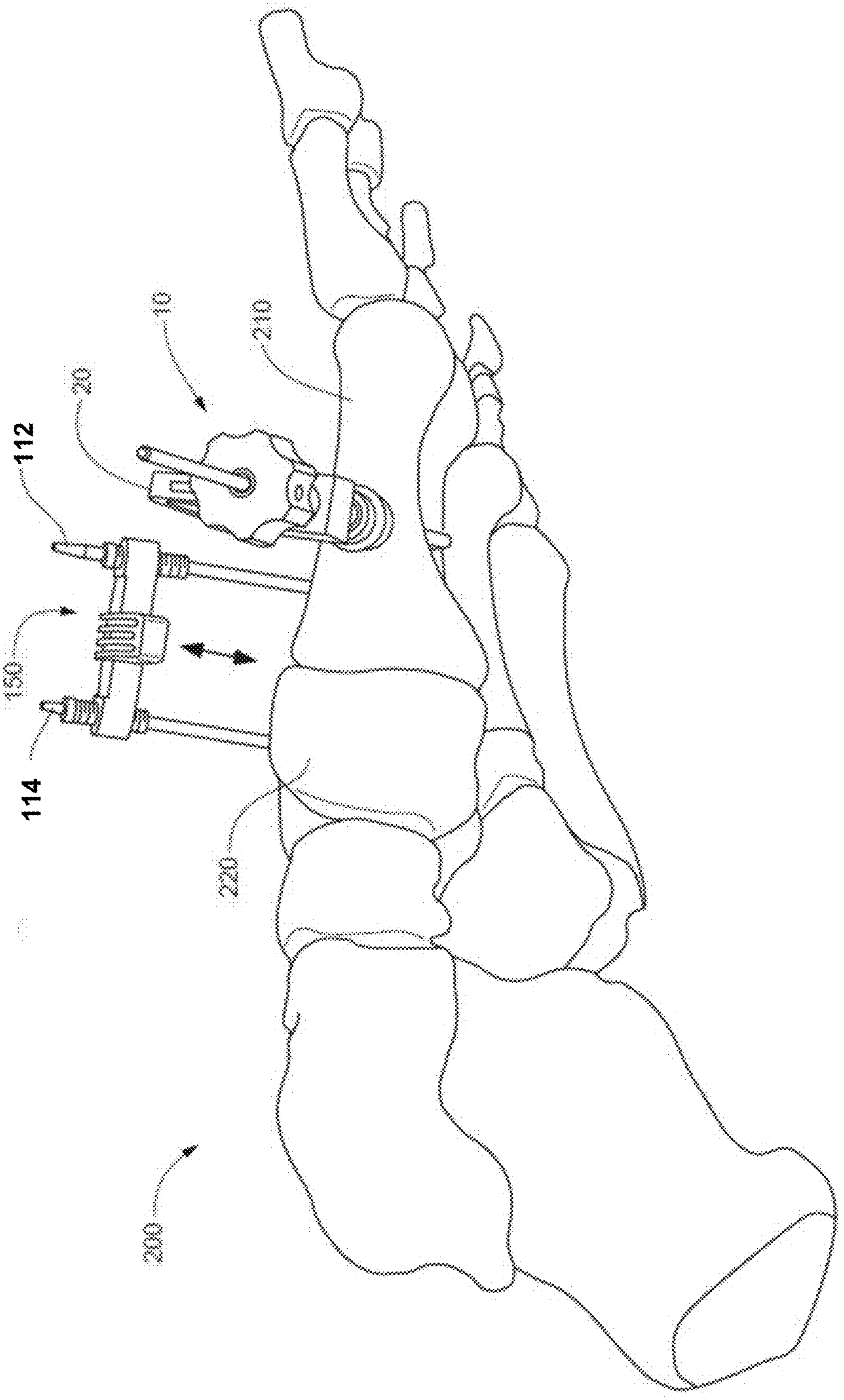
FIG. 14 is a perspective view of a foot depicting a removal of a bone preparation guide.
Figure 15:
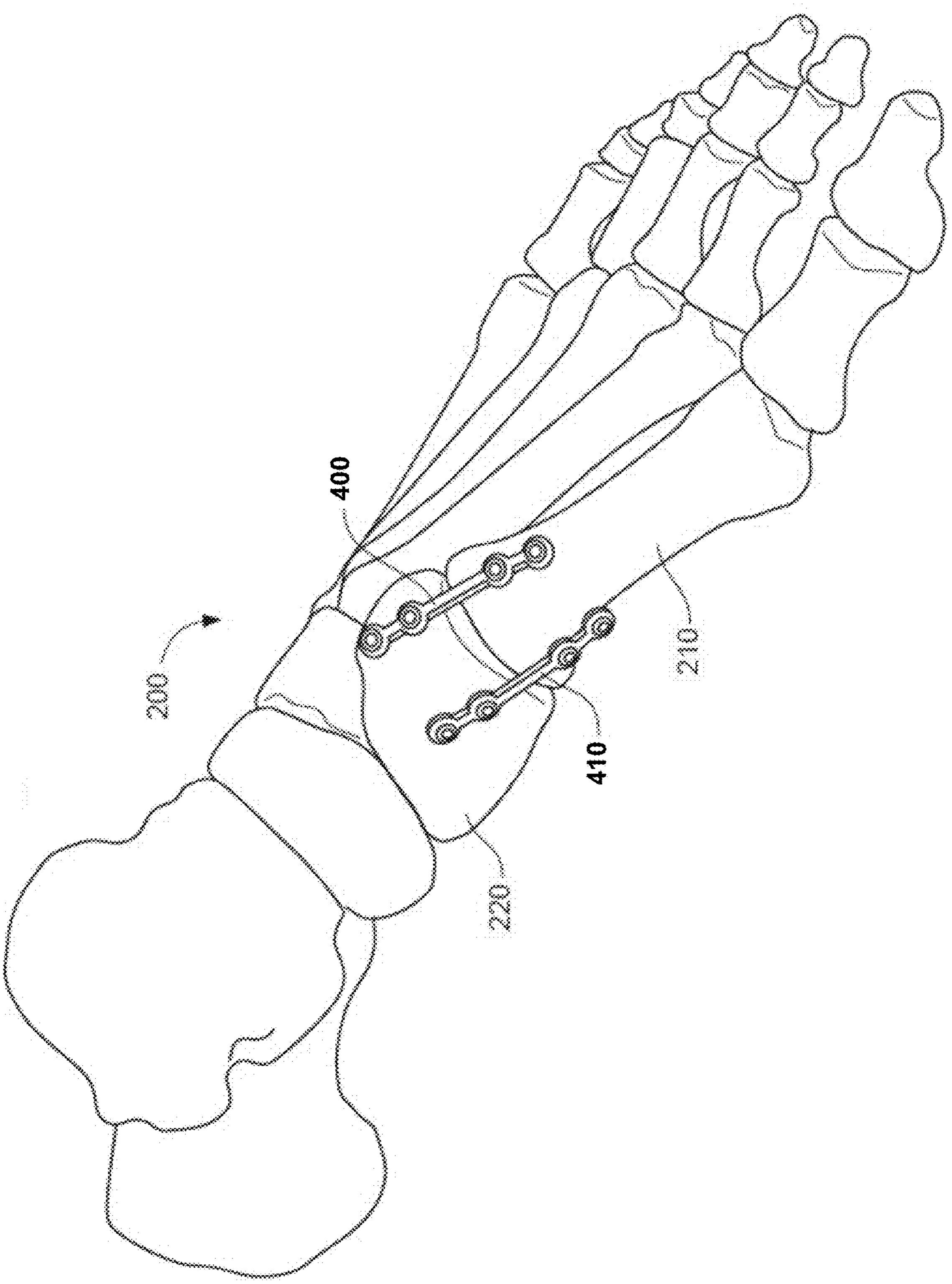
FIG. 15 is a side perspective view of a foot depicting bone plates across a joint between first and second bones.

Any angled/converging pins can be removed and the bone preparation guide 150 can be lifted off the substantially parallel first and second pins 112, 114, as shown in FIG. 14. In applications where bone positioning guide 10 is utilized, the bone positioning guide may be removed before or after bone preparation guide 150 is removed. In either case, in some examples, a temporary fixation pin 300 may be used to maintain the position of the underlying bones (e.g., first metatarsal 210 relative to medial cuneiform 222) while bone preparation guide 150 is removed and compressor-distractor 100 is installed.

With the end faces of the metatarsal and cuneiform optionally pressed together via a compressor-distractor, the clinician may provisionally or permanently fixate the bones or bones portions together. For example, one or more bone fixation devices can be applied across the joint and to the two bones to stabilize the joint for fusion, such as two bone plates positioned in different planes. FIG. 14 illustrates an example fixation device arrangement that includes a first bone plate 400 positioned on a dorsal-medial side of the first metatarsal and medial cuneiform and a second bone plate 410 positioned on a medial-plantar side of the first metatarsal and the medial cuneiform. In other embodiments, second bone plate 410 can be a helical bone plate positioned from a medial side of the cuneiform to a plantar side of the first metatarsal across the joint space. The plates can be applied with the insertion of bone screws. Example bone plates that can be used as first bone plate 400 and/or second bone plate 410 are described in US Patent Publication No. US2016/0192970, titled "Bone Plating System and Method" and filed Jan. 7, 2016, which is incorporated herein by reference. Other types in configurations of bone fixation devices can be used, and the disclosure is not limited in this respect. Any temporary fixation pins 300 inserted into the bones can be removed once permanent fixation is applied.

Multi-diameter fixation pins, along with associated techniques and systems, have been described. In some examples, a multi-diameter fixation pin according to the disclosure is included in a disposable, sterile kit that includes associated surgical instrumentation, such as bone positioning guide and/or a preparation guide described herein. Other components that may be included within the sterile kit include bone fixation devices, bone fixation screws, single diameter pins for insertion into pin-receiving holes, and the like.

Various examples have been described. These and other examples are within the scope of the following claims.

The invention claimed is:

1. A method comprising:

inserting a pin having a first diameter into a collet of a powered driver and driving the pin into a bone portion; and inserting a driver engagement portion of a multi-diameter fixation pin into the collet of the powered driver and driving a bone insertion portion of the multi-diameter fixation pin into the bone portion;

wherein the collet of the powered driver is sized to receive the pin having the first diameter and the driver engagement portion of the multi-diameter fixation pin but not the bone insertion portion of the multi-diameter fixation pin.

2. The method of claim 1, wherein the bone portion is a first bone portion, and inserting the pin having the first diameter into the collet of the powered driver and driving the pin into the bone portion comprises:

inserting a first pin having the first diameter into the collet of the powered driver and driving the first pin into the first bone portion, removing the first pin from the collet of the powered driver while the first pin remains in the first bone portion, inserting a second pin having the first diameter into the collet of the powered driver and driving the second pin into a second bone portion separated from the first bone portion by (a) a joint or (b) a cut dividing a bone into the first bone portion and the second bone portion; and removing the second pin from the collet of the powered driver while the second pin remains in the second bone portion.

3. The method of claim 1, wherein inserting the driver engagement portion of the multi-diameter fixation pin into the collet of the powered driver comprises inserting the multi-diameter fixation pin into the collet to a depth less than or equal to a depth denoted by an indicator on the multi-diameter fixation pin.

4. The method of claim 3, wherein the indicator comprises a notch formed into a perimeter surface of a body of the multi-diameter fixation pin.

5. The method of claim 1, wherein the first diameter and a diameter of the driver engagement portion each ranges from 2.0 mm to 3.2 mm, and a diameter of the bone insertion portion ranges from 0.7 mm to 1.8 mm.

6. The method of claim 1, wherein the first diameter and a diameter of the driver engagement portion each are greater than or equal to 2.0 mm, and a diameter of the bone insertion portion is less than 2.0 mm.

7. The method of claim 1, wherein driving the bone insertion portion of the multi-diameter fixation pin into the bone portion comprises driving the bone insertion portion of the multi-diameter fixation pin through the bone portion and into an adjacent bone portion.

8. The method of claim 1, wherein the bone portion comprises a metatarsal or a portion thereof.

9. The method of claim 8, further comprising moving the bone portion to correct a bunion deformity.

10. The method of claim 9, wherein moving the bone portion to correct the bunion deformity comprises moving the bone portion in a transverse plane and rotating the bone portion in a frontal plane.

11. The method of claim 8, wherein the metatarsal is a first metatarsal.

* * * * *